United States Patent [19]

Ono et al.

[11] Patent Number: 4,746,602
[45] Date of Patent: May 24, 1988

[54] SILVER HALIDE COLOR PHOTOGRAPHIC MATERIAL

[75] Inventors: Michio Ono; Kozo Aoki, both of Kanagawa, Japan

[73] Assignee: Fuji Photo Film Co., Ltd., Kanagawa, Japan

[21] Appl. No.: 44,270

[22] Filed: Apr. 30, 1987

[30] Foreign Application Priority Data

Apr. 30, 1986 [JP] Japan .................... 61-100222

[51] Int. Cl.⁴ .................................................. G03C 7/34
[52] U.S. Cl. ...................................... 430/549; 430/552; 430/553; 430/558
[58] Field of Search ............... 430/552, 553, 549, 558

[56] References Cited

U.S. PATENT DOCUMENTS

| 4,327,173 | 4/1982 | Aoki et al. | 430/553 |
| 4,430,423 | 2/1984 | Aoki et al. | 430/558 |
| 4,513,081 | 4/1985 | Okazaki et al. | 430/558 |
| 4,564,586 | 1/1986 | Aoki et al. | 430/553 |
| 4,621,047 | 11/1986 | Kishimoto et al. | 430/553 |
| 4,696,893 | 9/1987 | Umemoto et al. | 430/552 |

Primary Examiner—Paul R. Michl
Assistant Examiner—Mark R. Buscher

Attorney, Agent, or Firm—Sughrue, Mion, Zinn, Macpeak & Seas

[57] ABSTRACT

A silver halide color photographic material is disclosed, comprising a support having provided thereon at least one silver halide emulsion layer containing a cyan-dye-forming coupler represented by formula (I)

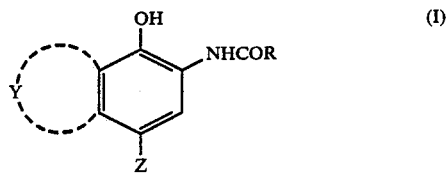

wherein Y represents an atomic group forming an at least 7-membered nitrogen-containing heterocyclic ring containing at least one —NHCO— group; Z represents a hydrogen atom or a group releasable upon coupling with an oxidation product of a color developing agent; R represents an aliphatic group, an aromatic group, a heterocyclic group, or a substituted amino group, or any of R, Z and Y form a dimer or higher polymer.

The material forms a dye image excellent in fastness and color reproducibility, and free from white background stains.

21 Claims, No Drawings

SILVER HALIDE COLOR PHOTOGRAPHIC MATERIAL

FIELD OF THE INVENTION

This invention relates to a silver halide color photographic material containing a novel cyan dye forming coupler.

BACKGROUND OF THE INVENTION

Dye image formation in silver halide light-sensitive materials is effected by exposure to light and color development processing in which a developing agent, e.g., aromatic primary amines, oxidized with silver halide is allowed to react with a dye forming coupler. In this image formation system, color reproduction is generally achieved by a subtractive color process, in which blue, green, and red colors are reproduced by forming the complementary colors, i.e., yellow, magenta, and cyan dyes, respectively.

Cyan dye forming couplers (also typically referred to more simply as "cyan couplers") widely employed include phenol couplers and naphthol couplers. However, dye images obtained from the conventionally employed phenol and naphthol couplers have some problems remaining unsolved in terms of preservability. For example, dye images obtained from 2-acylaminophenol cyan couplers as described in U.S. Pat. Nos. 2,367,531, 2,369,929, 2,423,730, 2,801,171, etc., are generally inferior in fastness to heat; those obtained from 2,5-diacylaminophenol cyan couplers as described in U.S. Pat. Nos. 2,772,162 and 2,895,826 are generally inferior in fastness to light; and those obtained from 1-hydroxy-2-naphthamide cyan couplers are generally insufficient in fastness to both light and heat, particularly wet heat.

5-Hydroxy-6-acylaminocarbostyril cyan couplers described in U.S. Pat. Nos. 4,327,173 and 4,564,586, and 4-hydroxy-5-acylamino-oxyindole couplers, 4-hydroxy-5-acylamino-2,3-dihydro-1,3-benzimidazol-2-one couplers, etc., described in U.S. Pat. No. 4,430,423 are excellent in light and heat fastness, but are disadvantageous in that the white background in unexposed areas undergoes yellow staining.

SUMMARY OF THE INVENTION

One object of this invention is to provide a color photographic material using a cyan dye forming coupler which forms a dye image excellent in fastness and color reproducibility and free from white background stains.

Another object of this invention is to provide a cyan coupler which shows high rates of dye formation and high maximum color densities in a color developer, and particularly a color developer containing no benzyl alcohol.

A further object of this invention is to provide a cyan coupler which undergoes substantially no reduction in density even when processed with a bleaching solution with weak oxidizing capacity, such as a bleaching solution containing a sodium (ethylenediaminetetraacetato)iron (III) or ammonium (ethylenediaminetetraacetato)iron (III), or a bleaching solution suffering from fatigue.

It has now been found that these objects can be accomplished by a coupler represented by formula (I)

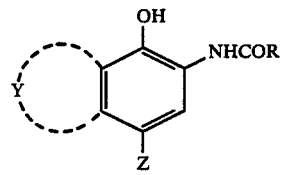

wherein Y represents an atomic group forming an at least 7-membered nitrogen-containing heterocyclic ring containing at least one —NHCO— group; Z represents a hydrogen atom or a group releasable upon coupling with an oxidation product of a color developing agent; R represents an aliphatic group, an aromatic group, a heterocyclic group, or a substituted amino group; or any of R, Z and Y form a dimer or higher polymer.

DETAILED DESCRIPTION OF THE INVENTION

In formula (I), Y represents an atomic group forming a 7-or more membered nitrogen-containing heterocyclic ring containing at least one —NHCO— group. Divalent groups forming such a ring, in addition to an —NHCO— group, include a substituted or unsubstituted amino group, an ether linkage, a thiol linkage, a substituted or unsubstituted alkylene group, an ethylene linkage, an imino linkage, a substituted or unsubstituted sulfonyl group, a carboxyl group, and a group represented by formula

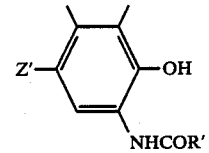

wherein Z' has the same meaning as Z (Z and Z' may be the same or different); and R' has the same meaning as R (R and R' may be the same or different), and includes combinations of these divalent groups. Substituents for these groups are the same as enumerated for substituents for R hereinafter described.

R in formula (I) represents a substituted or unsubstituted cyclic or acyclic aliphatic group (preferably having from 1 to 32 carbon atoms), e.g., a methyl group, a butyl group, a pentadecyl group, a cyclohexyl group, an allyl group, etc.; a substituted or unsubstituted aromatic group, e.g., a phenyl group, a naphthyl group, etc.; a substituted or unsubstituted heterocyclic group, e.g., a 2-, 3-, or 4-pyridyl group, a 2-furanyl group, a 2-oxazolyl group, etc.; or a substituted amino group. Substituents for these groups include an alkyl group, an aryl group (e.g., a phenyl group, a naphthyl group, etc.), an alkyloxy group (e.g., a methoxy group, a myristyloxy group, a methoxyethyloxy group, etc.), an aryloxy group (e.g., a phenyloxy group, a 2,4-di-t-amylphenoxy group, a 3-t-butyl-4-hydroxyphenyloxy group, a naphthyloxy group, etc.), a carboxyl group, an alkylcarbonyl group (e.g., an acetyl group, a tetradecanoyl group, etc.), an arylcarbonyl group (e.g., a benzoyl group, etc.), an alkoxycarbonyl group (e.g., a methoxycarbonyl group, a benzyloxycarbonyl group, etc.), an aryloxycarbonyl group (e.g., a phenyloxycarbonyl group, a p-tolyloxycarbonyl group, etc.), an acyloxy group (e.g., an acetyl group, a benzoyloxy group, a phenylaminocarbonyloxy group, etc.), a sulfamoyl group (e.g., an N-ethylsulfamoyl group, an N-octadecylsulfamoyl group, etc.), a carbamoyl group (e.g., an N-ethylcarbamoyl group, an N-methyldodecylcarbamoyl group, etc.), a sulfonamido group (e.g., a methanesulfonamido group, a benzenesulfonamido group, an ethylaminosulfonamido group, etc.), an acylamino group (e.g., an acetylamino group, a benzamido group, an ethoxycarbonylamino group, a phenylaminocarbonylamino group, etc.), a diacylamino group (e.g., a succinimido group, a hydantoinyl group, etc.), a sulfonyl group (e.g., a methanesulfonyl group, etc.), a hydroxyl group, a cyano group, a nitro group, and a halogen atom.

Z in formula (I) represents a hydrogen atom or a coupling releasable group. Examples of the releasable group are a halogen atom (e.g., a fluorine atom, a chlorine atom, a bromine atom), an alkoxy group (e.g., an ethoxy group, a dodecyloxy group, a methoxyethylcarbamoylmethoxy group, a carboxypropyloxy group, a methylsulfonylethoxy group, etc.), an aryloxy group (e.g., a 4-chlorophenoxy group, a 4-methoxyphenoxy group, a 4-carboxyphenoxy group, etc.), an acyloxy group (e.g., an acetoxy group, a tetradecanoyloxy group, a benzoyloxy group, etc.), a sulfonyloxy group (e.g., a methanesulfonyloxy group, a toluenesulfonyloxy group, etc.), an amido group (e.g., a dichloroacetylamino group, a heptafluorobutyrylamido group, a methanesulfonylamino group, a toluenesulfonylamino group, etc.), an alkoxycarbonyloxy group (e.g., an ethoxycarbonyloxy group, a benzyloxycarbonyloxy group, etc.), an aryloxycarbonyloxy group (e.g., a phenoxycarbonyloxy group, etc.), an aliphatic or aromatic thio group (e.g., an ethylthio group, a phenylthio group, a tetrazolylthio group, etc.), an imido group (e.g., a succinimido group, a hydantoinyl group, etc.), an aromatic azo group (e.g., a phenylazo group, etc.), and the like. These releasable groups may contain a photographically useful group.

Preferred of the groups represented by Z are a hydrogen atom, a halogen atom, an aryloxy group, an alkoxy group, and a sulfonamido group. Most preferred are a fluorine atom and a chlorine atom.

R or Z may be a divalent group forming a bis compound. Further, the couplers of the present invention may be in the form of a polymer containing a moiety represented by formula (I) pendent on its main chain or side chain. In particular, polymers derived from an ethylenically unsaturated compound including the moiety of formula (I) (hereinafter referred to as vinyl monomer) are preferred. In this case, the substituent represented by R, Z or Y forms a repeating unit contained in the polymeric main chain and its linking moiety.

When R or Z is a divalent group forming a bis compound, R preferably represents a substituted or unsubstituted alkylene group (e.g., a methylene group, an ethylene group, a 1,10-decylene group, —CH$_2$CH$_2$—O—CH$_2$CH$_2$—, etc.), a substituted or unsubstituted phenylene group (e.g., a 1,4-phenylene group, a 1,3-phenylene group,

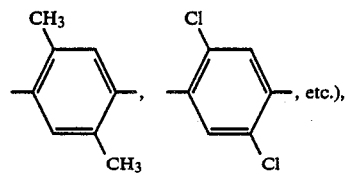

—NHCO—L—CONH— (wherein L represents a substituted or unsubstituted alkylene group or a substituted or unsubstituted phenylene group) (e.g., —NHCOCH$_2$CH$_2$CONH—,

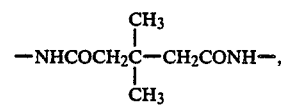

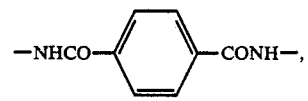

etc.), or —S—L—S— (wherein L represents a substituted or unsubstituted alkylene group) (e.g., —S—CH$_2$CH$_2$—S—,

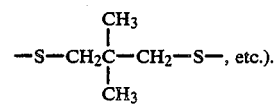

When the moiety of formula (I) is contained in a vinyl monomer, the linking group represented by R or Z and the linking group connecting the vinyl monomer and Y include a substituted or unsubstituted alkylene group (e.g., a methylene group, an ethylene group, a 1,10-decylene group, —CH$_2$CH$_2$OCH$_2$CH$_2$—, etc.), a substituted or unsubstituted phenylene group (e.g., a 1,4-phenylene group, a 1,3-phenylene group,

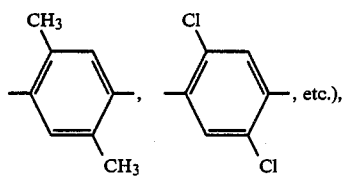

—NHCO—, —CONH—, —O—, —OCO—, a substituted or unsubstituted aralkylene group (e.g.,

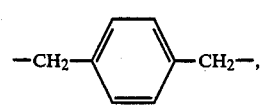

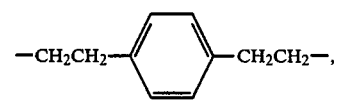

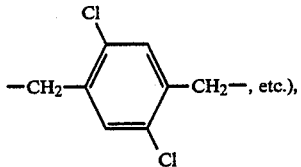

and combinations thereof.

Preferred linking groups are —NHCO—, —CH$_2$CH$_2$—,

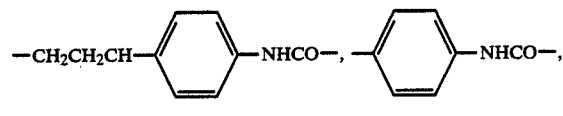

—CH$_2$CH$_2$NHCO—, $$-\text{CH}_2\text{CH}_2-\text{O}-\underset{\underset{\text{O}}{\|}}{\text{C}}-,$$

—CONH—CH$_2$CH$_2$NHCO—, —CH$_2$CH$_2$O—CH$_2$CH$_2$—NHCO—, and

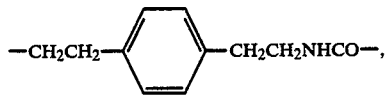

The vinyl group in the vinyl monomer may contain substituents other than those represented by formula (I). Preferred substituents are a hydrogen atom, a chlorine atom, and a lower alkyl group having up to 4 carbon atoms (e.g., a methyl group, an ethyl group, etc.).

The polymeric couplers may be copolymers comprising the monomer containing the moiety represented by formula (I) and a non-color-forming ethylenically unsaturated monomer incapable of coupling with an oxidation product of an aromatic primary amine developing agent.

Examples of such a non-color-forming ethylenically unsaturated monomer include acrylic acid, α-chloroacrylic acid, an α-alacrylic acid (e.g., methacrylic acid) and esters or amides thereof (e.g., acrylamide, n-butylacrylamide, t-butylacrylamide, diacetonacrylamide, methacrylamide, methyl acrylate, ethyl acrylate, n-propyl acrylate, n-butyl acrylate, t-butyl acrylate, isobutyl acrylate, 2-ethylhexyl acrylate, n-octyl acrylate, lauryl acrylate, methyl methacrylate, ethyl methacrylate, n-butyl methacrylate, β-hydroxy methacrylate, etc.), methylenedibisacrylamide, vinyl esters (e.g., vinyl acetate, vinyl propionate, vinyl laurate, etc.), acrylonitrile, methacrylonitrile, aromatic vinyl compounds (e.g., styrene and derivatives thereof, vinyltoluene, divinylbenzene, vinylacetophenone, sulfostyrene, etc.), itaconic acid, citraconic acid, crotonic acid, vinylidene chloride, vinyl alkyl ethers (e.g., vinyl ethyl ether, etc.), maleic acid, maleic anhydride, maleic esters, N-vinyl-2-pyrrolidone, N-vinylpyridine, 2- or 4-vinylpyridine, and the like. These non-color-forming ethylenically unsaturated monomers may be used in combinations of two or more thereof. Such monomer combinations include n-butyl acrylate/methyl acrylate, styrene/methacrylic acid, methacrylic acid/acrylamide, methyl acrylate/diacetonacrylamide, and the like.

As is well known in the art, non-color-forming ethylenically unsaturated monomers to be copolymerized with solid, water-insoluble monomeric couplers can be selected so that the selected comonomer may exert favorable influences on physical and/or chemical properties of the resulting copolymer, such as solubility, compatibility with binders for photographic colloidal compositions, e.g., gelatin, flexibility, thermal stability, and the like.

The polymeric couplers which can be used in the present invention may be either water-soluble or water-insoluble. Polymeric coupler latices are particularly preferred.

Of the compounds represented by formula (I), preferred are those represented by formulae (II) and (III) shown below.

Formula (II) is represented by

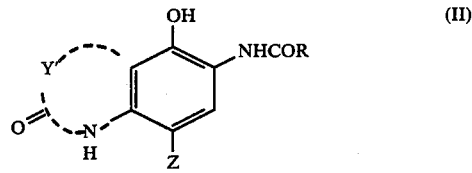

wherein Y' represents an atomic group forming an at least 7-membered nitrogen-containing heterocyclic ring together with the atomic group to which Y' is bonded; and R and Z each has the same meaning as defined above.

Formula (III) is represented by

wherein R, Z and Y' are as defined above.

Examples of the divalent group forming the aforesaid heterocyclic ring include a substituted or unsubstituted divalent amino group, an ether linkage, a thiol linkage, a substituted or unsubstituted alkylene group, an ethylene linkage, an imino linkage, a substituted or unsubstituted sulfonyl group, a substituted or unsubstituted carbonyl group, a group of formula

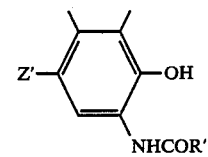

(wherein R' and Z' are as defined above), etc., and combinations thereof.

The number of members constituting the rings of formulae (II) and (III) is preferably 7 or 8.

Preferred examples of the atomic group as represented by Y' are shown below.

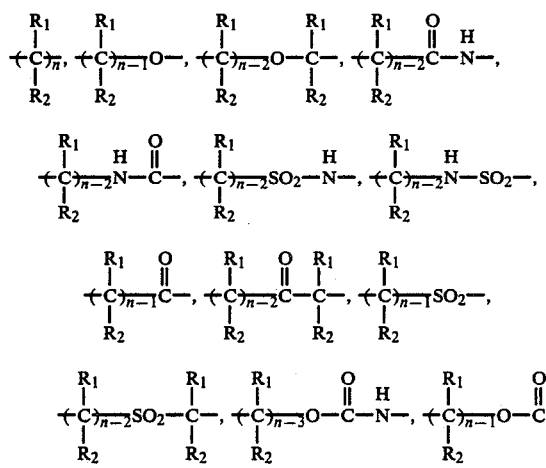

wherein $R_1$ and $R_2$ each represents a hydrogen atom, a halogen atom, an alkyl group (e.g., a methyl group, a butyl group, etc.), an aryl group (e.g., a phenyl group, a naphthyl group, etc.), an alkyloxy group (e.g., a methoxy group, a dodecyloxy group, etc.), an alkyloxycarbonyl group (e.g., a methoxycarbonyl group, a tetradecyloxycarbonyl group, etc.), an alkylcarbonyl group (e.g., an acetyl group, a butanoyl group, etc.), an arylcarbonyl group (e.g., a benzoil group, etc.), a carbamoyl group (e.g., an N-ethylcarbamoyl group, etc.), an acylamino group (e.g., an acetylamino group, an N-methylbenzoylamino group, etc.), or a nitrile group, or $R_1$ and $R_2$ or a substituent on the adjacent carbon atom are taken together to form a ring or a double bond; and n represents 3 or 4.

Particularly preferred of the compounds of formula (I) are those represented by formula (IV)

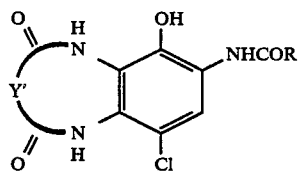

wherein Y″ represents an atomic group forming a 7- to 16-membered nitrogen-containing heterocyclic group together with the atomic group to which Y″ is bonded; and R is the same as defined above.

Examples of the divalent groups forming the aforesaid heterocyclic ring of formula (IV) include a substituted or unsubstituted divalent amino group, an ether linkage, a thiol linkage, a substituted or unsubstituted alkylene group, an ethylene linkage, an imino linkage, a substituted or unsubstituted sulfonyl group, a substituted or unsubstituted carbonyl group, a group of the formula

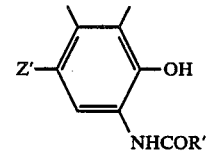

(wherein Z′ and R′ are the same as defined above), etc., and combinations thereof.

Y″ in formula (IV) preferably represents

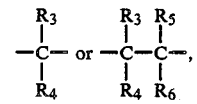

wherein $R_3$, $R_4$, $R_5$ and $R_6$ each represents a hydrogen atom, a halogen atom, an alkyl group (e.g., a methyl group, butyl group, etc.), an aryl group (e.g., a phenyl group, naphthyl group, etc.), an alkyloxy group (e.g., a methoxy group, or dodecyloxy group, etc.), an alkyloxycarbonyl group (e.g., a methoxycarbonyl group, a tetradecyloxycarbonyl group, etc.), an alkylcarbonyl group (e.g., an acetyl group, a butanoyl group, etc.), an arylcarbonyl group (e.g., a benzoyl group, etc.), a carbamoyl group (e.g., an N-ethylcarbamoyl group, etc.), an acylamino group (e.g., an acetylamino group, an N-methylbenzoylamino group, etc.), or a nitrile group, or $R_3$ and $R_4$, or $R_3$ and $R_5$ together form a ring or a double bond, or $R_3$, $R_4$, $R_5$ and $R_6$ together form an aromatic ring.

Specific examples of the compounds represented by formula (I) are listed below, but the present invention is not limited thereto. In the following formulae, the copolymerization ratios are given by weight.

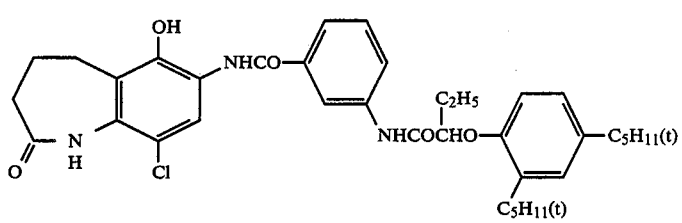

(1)

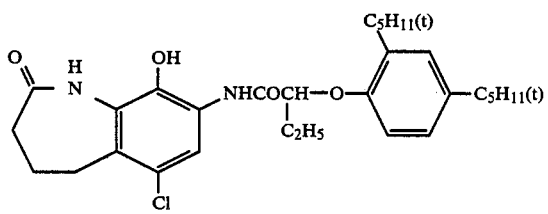

(2)

-continued
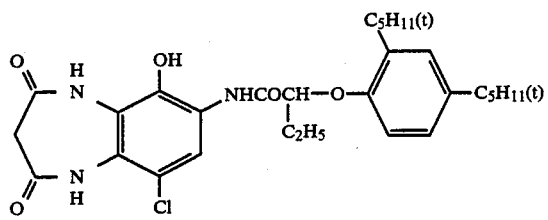 (3)
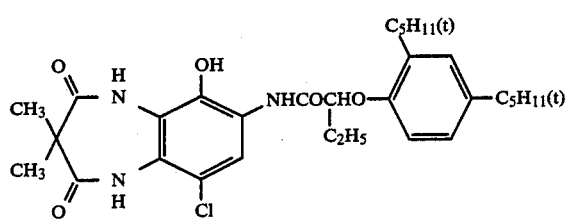 (4)
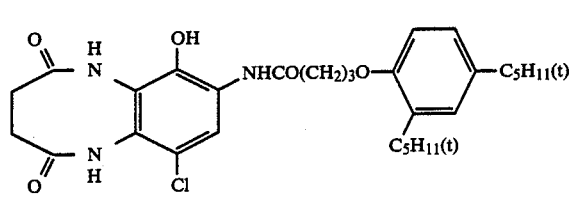 (5)
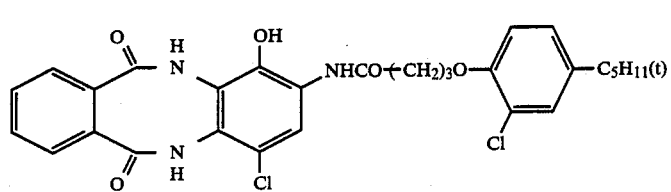 (6)
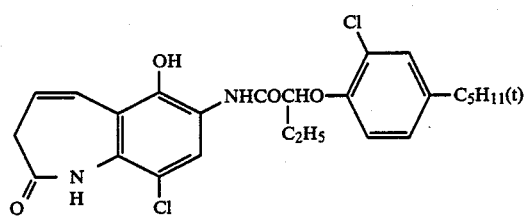 (7)
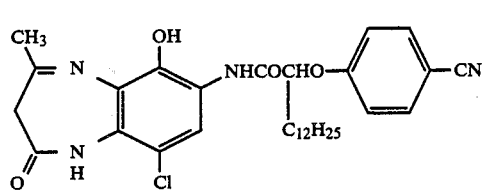 (8)
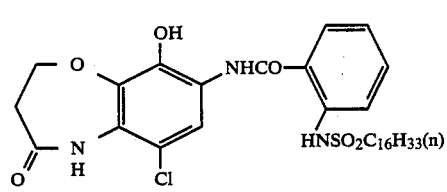 (9)
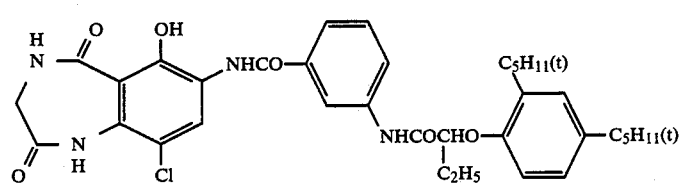 (10)

-continued
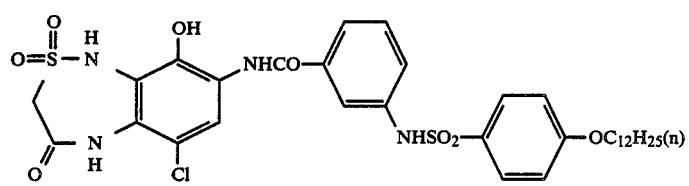 (11)
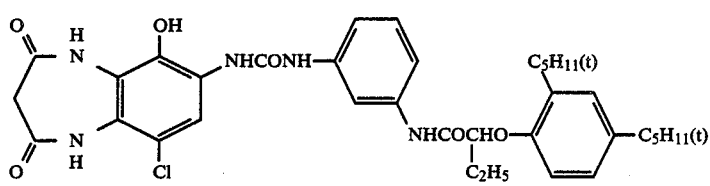 (12)
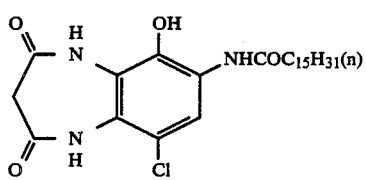 (13)
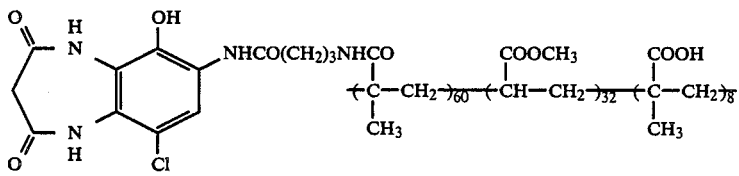 (14)
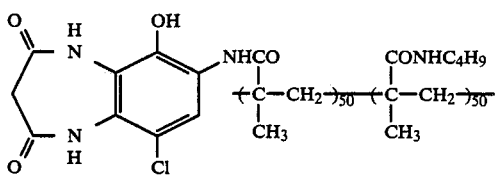 (15)
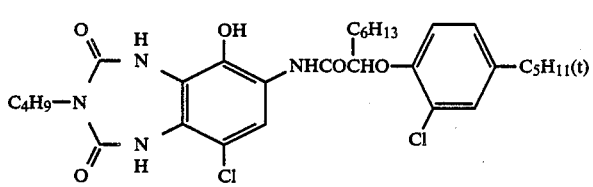 (16)
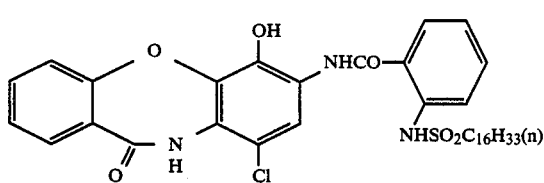 (17)
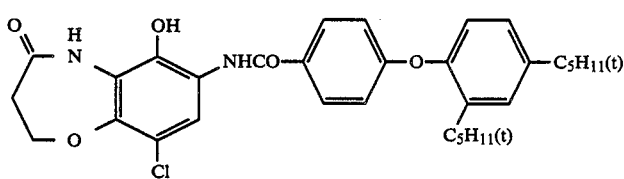 (18)

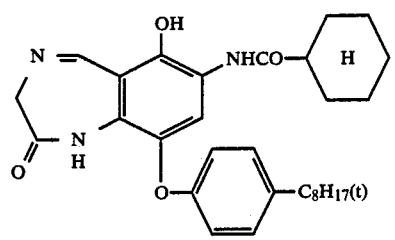 (19)

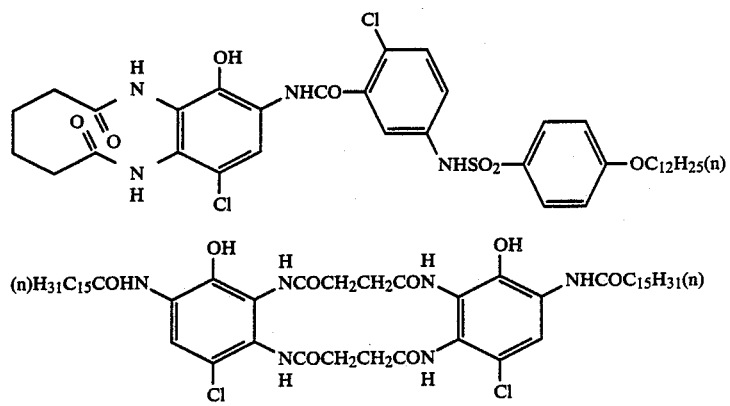 (20)

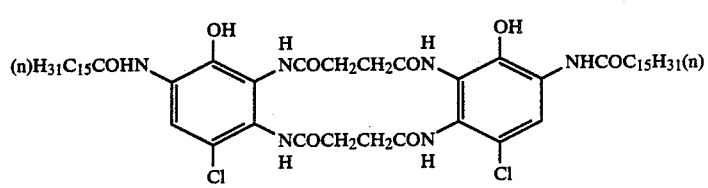 (21)

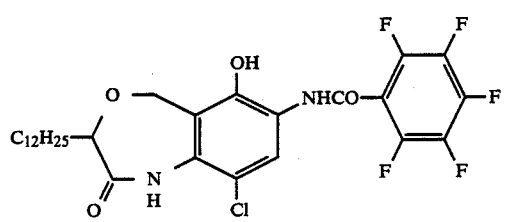 (22)

Typical synthesis examples of the couplers in accordance with the present invention are described below.

SYNTHESIS EXAMPLE 1

Synthesis of 9-Chloro-7-{3-[2-(2,4-di-t-amylphenoxy)-butanoylamino]benzoylamino}-6-hydroxybenzazepin-2-one (Coupler 1)

(1) Synthesis of 5-Methoxytetalone Oxime:

In a mixture of 240 ml of ethanol and 80 ml of water were dispersed 50 g of 5-methoxytetralone, 20 g of hydroxylamine hydrochloride, and 56 g of sodium acetate, and the dispersion was heat-refluxed for 4 hours. After cooling to room temperature, the reaction mixture was poured into 400 ml of water. The precipitated crystals were collected by filtration and dried to obtain 53 g of 5-methoxytetralone oxime.

(2) Synthesis of 6-Methoxybenzazepin-2-one:

50 g of the resulting 5-methoxytetralone oxime was dispersed in 350 g of polyphosphoric acid, and the dispersion was heated on a steam bath for 30 minutes. The reaction mixture was poured into ice-water, and the precipitated crystals were collected by filtration and dried to obtain 45 g of the desired compound.

(3) Synthesis of 6-Hydroxybenzazepin-2-one:

In 100 ml of methylene chloride was dissolved 25 g of the resulting 6-methoxybenzazepin-2-one, and 66 g of boron tribromide was added thereto dropwise at room temperature over 20 minutes. After stirring at room temperature for 1 hour, the reaction mixture was poured into ice-water, and the precipitated crystals were collected by filtration, washed with water, and dried to provide 18 g of 6-hydroxybenzazepin-2-one.

(4) Synthesis of 7-Nitro-6-hydroxybenzazepin-2-one:

In 150 ml of acetic anhydride was dispersed 17 g of the 6-hydroxybenzazepin-2-one, and a solution of 7.3 ml of nitric acid (d=1.40) in 15 ml of acetic acid was added to the dispersion dropwise over a period of 10 minutes under ice-cooling. After stirring for 3 hours under ice-cooling, the reaction mixture was poured into ice-water. The crystals were collected by filtration and dried to yield 17 g of crude crystals. Recrystallization from methanol gave 7 g of the desired compound.

(5) Synthesis of 7-Amino-6-hydroxybenzazepin-2-one:

7 g of the resulting 7-nitro-6-hydroxybenzazepin-2-one was dispersed in 50 ml of water, and to the dispersion was slowly added 30 g of sodium hydrosulfite while heating on a steam bath. After refluxing, the reaction mixture was cooled and the precipitated crystals were collected by filtration and dried to obtain 4 g of 7-amino-6-hydroxybenzazepin-2-one.

(6) Synthesis of 7-{3-[2-(2,4-Di-t-amylphenoxy)-butanoylamino]benzoylamino}-6-hydroxybenzazepin-2-one:

In 20 ml of benzene was dissolved 9.6 g of 3-[2-(2,4-di-t-amylphenoxy)butanoylamino]benzoic acid, and 5 ml of thionyl chloride was added thereto, followed by heat-refluxing for 1 hour. The reaction mixture was concentrated under reduced pressure. To the residue were added 30 ml of acetonitrile, 5 ml of dimethylacetamide, and the 7-amino-6-hydroxybenzazepin-2-one prepared in (5) above, and the mixture was heat-refluxed for 1 hour. The reaction mixture was cooled to room temperature, and 5 ml of water was added thereto, followed by stirring. The precipitated crystals were collected by filtration, washed with acetonitrile, and dried to obtain 6.8 g of the desired compound.

(7) Synthesis of 9-Chloro-7-{3-[2-(2,4-di-t-amylphenoxy)butanoylamino]benzoylamino}-6-hydroxybenzazepin-2-one:

In 30 ml of methylene chloride was dispersed 6 g of the 7-{3-[2-(2,4-di-t-amylphenoxy)butanoylamino]benzoylamino}-6-hydroxybenzazepin-2-one prepared in (6) above, and 0.84 ml of sulfuryl chloride was added dropwise to the dispersion at room temperature. After stirring at room temperature for 2 hours, ethyl acetate and a saturated aqueous solution of sodium chloride were added thereto to effect extraction. The extract was concentrated under reduced pressure, and the residue was dispersed in 30 ml of acetonitrile and 15 ml of ethyl acetate. The dispersion was heat-refluxed, followed by cooling. The precipitated crystals were collected by filtration and dried to obtain 5.8 g of the desired coupler having a melting point of 234° to 236° C.

| | Elementary Analysis: | | |
|---|---|---|---|
| | C | H | N |
| Found (%): | 68.50 | 7.11 | 6.53 |
| Calc'd (%): | 68.56 | 7.15 | 6.48 |

SYNTHESIS EXAMPLE 2

Synthesis of 9-Chloro-7-[2-(2,4-di-t-amylphenoxy)butanoylamino]-6-hydroxy-1,5-benzodiazepin-2,4-dione (Coupler 3)

(1) Synthesis of 5-Amino-4-chloro-2-[2-(2,4-di-t-amylphenoxy)butanoylamino]phenol:

20 g of 2-amino-4-chloro-5-nitrophenol was dispersed in 150 ml of acetonitrile, and 37.7 g of 2-(2,4-di-t-amylphenoxy)butanoyl chloride was added thereto dropwise under refluxing. After stirring while refluxing for 1 hour, the reaction mixture was cooled to room temperature, and the crystals thus formed were collected by filtration, washed with acetonitrile, and dried to obtain crystals weighing 49.5 g. A mixture of 49 g of the resulting crystals, 28 g of reduced iron, 2.7 g of ammonium chloride, 50 ml of water, and 500 ml of isopropanol was stirred while refluxing for 1 hour. The iron powder was removed by filtration, and the filtrate was cooled to precipitate crystals, which were then collected by filtration and dried to provide 42.4 g of the desired compound.

(2) Synthesis of 5-Acetylamino-4-chloro-2-[2-(2,4-di-t-anylphenoxy)butanoylamino]phenol:

In a mixture of 160 ml of acetonitrile and 20 ml of dimethylacetamide was dispersed 40 g of the 5-amino-4-chloro-2-[2-(2,4-di-t-amylphenoxy)butanoylamino]phenol prepared in (1) above, and 6.6 ml of acetyl chloride was added dropwise thereto while refluxing. After stirring while refluxing for 1 hour, the reaction mixture was cooled. The precipitated crystals were collected by filtration and dried to provide 40.8 g of the desired compound.

(3) Synthesis of 3-Acetylamino-4-chloro-2-nitro-6-[2-(2,4-di-t-amylphenoxy)butanoylamino]phenol:

In 200 ml of chloroform was dispersed 40 g of the 5-acetylamino-4-chloro-2-[2-(2,4-di-t-amylphenoxy)-butanoylamino]phenol prepared above, and 15.5 ml of nitric acid was added dropwise to the dispersion under ice-cooling. After stirring at room temperature for 2 hours, 300 ml of water was added, and the mixture was extracted with chloroform. The chloroform extract was washed with water, followed by concentration. The residue was crystallized from acetonitrile and dried to yield 41 g of the desired compound.

(4) Synthesis of 3-Amino-4-chloro-2-nitro-6-[2-(2,4-di-t-amylphenoxy)butanoylamino]phenol:

In 200 ml of methanol was dispersed 40 g of the 3-acetylamino-4-chloro-2-nitro-6-[2-(2,4-di-t-amylphenoxy)butanoylamino]phenol, and the dispersion was stirred while refluxing for 5 hours together with 9 g of sodium hydroxide and 40 ml of water. The reaction mixture was cooled to room temperature and then poured into 300 ml of water. Upon dropwise addition of 15 ml of acetic acid, red crystals were precipitated. The crystals were collected by filtration, recrystallized from acetonitrile, and dried to provide 21 g of the desired compound.

(5) Synthesis of 2,3-Diamino-4-chloro-6-[2-(2,4-di-t-amylphenoxy)butanoylamino]phenol:

In a mixture of 200 ml of water and 40 ml of isopropanol was dispersed 20 g of the 3-amino-4-chloro-2-nitro-6-[2-(2,4-di-t-amylphenoxy)butanoylamino]phenol prepared in (4) above, and 100 g of sodium hydrosulfite was slowly added to the dispersion while stirring and heating on a steam bath. After refluxing, the reaction mixture was concentrated, and the precipitated solid was collected by filtration, washed with water, and dried to provide 17 g of the desired compound.

(6) Synthesis of 9-Chloro-7-[2-(2,4-di-t-amylphenoxy)butanoylamino]-6-hydroxy-1,5-benzodiazepin-2,4-dione:

In 250 ml of benzene was dissolved 17 g of the resulting 2,3-diamino-4-chloro-6-[2-(2,4-di-t-amylphenoxy)-butanoylamino]phenol, and a solution of 5.8 g of malonyl dichloride in 100 ml of benzene was slowly added to the solution at room temperature while stirring. After the dropwise addition, the reaction mixture was stirred for 1 hour. Water and ethyl acetate were added to the reaction mixture to effect extraction. The extract was concentrated, and the residue was purified by silica gel column chromatography (chloroform/ethyl acetate=2/1 by volume) to obtain 4.2 g of the desired coupler (Coupler 3) having a melting point of 193° to 195° C.

| | Elementary Analysis: | | |
|---|---|---|---|
| | C | H | N |
| Found (%): | 63.99 | 7.01 | 7.80 |
| Calc'd (%): | 64.02 | 7.04 | 7.72 |

SYNTHESIS EXAMPLE 3

Synthesis of 9-Chloro-7-(4-methacrylamidobutanamido)-6-hydroxy-1,5-benzodiazepin-2,4-dione/Methacrylic Acid/Methyl Acrylate (Coupler 14)

(I) Synthesis of 9-Chloro-7-(4-methacrylamidobutanamido)-6-hydroxy-1,5-benzazepin-2,4-dione (monomeric coupler):

(1) Synthesis of 9-Chloro-7-(4-methacrylamidobutanamido)-6-hydroxy-1,5-benzazepin-2,4-dione:

In 500 ml of acetonitrile and 50 ml of dimethylacetamide was dispersed 100 g of 2-amino-4-chloro-5-nitrophenol, and 41.6 g of acetyl chloride was added dropwise thereto at reflux. After stirring while refluxing for 1 hour, the reaction mixture was cooled to room temperature. The precipitated crystals were collected by filtration, washed with acetonitrile, and dried to obtain crystals weighing 98 g.

The resulting crystals (98 g), 95 g of reduced iron, 10 g of ammonium chloride, 100 ml of water, and 500 ml of isopropanol were stirred while refluxing for 1 hour. After cooling to room temperature, 34 g of sodium hydroxide and 200 ml of water were added thereto to dissolve the crystals. The iron powder was removed by filtration, and 60 g of acetic acid was added to the filtrate. The precipitated crystals were collected by filtration and dried to obtain 78 g of the desired compound.

(2) Synthesis of 2,5-Diacetylamino-4-chlorophenol:

In 400 ml of the acetonitrile and 40 ml of dimethylacetamide was dispersed 78 g of the resulting 2-acetylamino-5-amino-4-chlorophenol, and 31 g of acetyl chloride was added dropwise to the dispersion while refluxing. After stirring while refluxing for 1 hour, the reaction mixture was cooled to room temperature. The precipitated crystals were collected by filtration, washed with acetonitrile, and dried to obtain 85 g of the desired compound.

(3) Synthesis of 3,6-Diacetylamino-4-chloro-2-nitrophenol:

In 500 ml of chloroform was dispersed 85 g of the resulting 2,5-diacetylamino-4-chlorophenol, and 29 ml of nitric acid was added thereto dropwise under ice-cooling. After stirring for 3 hours under ice-cooling, the precipitated crystals were filtered, washed with water, and dried to yield 95 g of the desired compound.

(4) Synthesis of 6-Acetylamino-3-amino-4-chloro-2-nitrophenol:

In 400 ml of methanol was dispersed 95 g of the resulting 3,6-diacetylamino-4-chloro-2-nitrophenol, and the dispersion was stirred for 10 hours under heating together with 40 g of sodium hydroxide and 80 ml of water. The reaction mixture was cooled to room temperature and then poured into 50 ml of water. Dropwise addition of 60 ml of acetic acid to the mixture precipitated red crystals, which were collected by filtration, washed with acetonitrile, and dried to obtain 60 g of the desired compound.

(5) Synthesis of 6-Acetylamino-2,3-diamino-4-chlorophenol:

In 600 ml of water was dispersed 60 g of the resulting 6-acetylamino-3-amino-4-chloro-2-nitrophenol, and 300 g of sodium hydrosulfite was slowly added thereto while stirring and heating on a steam bath. After completion of the refluxing, the precipitated crystals were collected by filtration, washed with water, and dried to yield 51 g of the desired compound.

(6) Synthesis of 7-Acetylamino-9-chloro-6-hydroxy-1,5-benzazepin-2,4-dione:

50 g of the resulting 6-acetylamino-2,3-diamino-4-chlorophenol was dissolved in 300 ml of acetonitrile and 300 ml of dimethylacetamide, and 33 g of malonyl dichloride was slowly added to the solution dropwise at room temperature while stirring, followed by stirring for 30 minutes. The reaction mixture was poured into 300 ml of water, and the precipitated crystals were filtered, recrystallized from acetonitrile, and dried to yield 28 g of the desired compound.

(7) Synthesis of 7-Amino-9-chloro-6-hydroxy-1,5-benzazepin-2,4-dione Hydrochloride:

In 50 ml of ethanol and 25 ml of water was dispersed 28 g of the resulting 7-acetylamino-9-chloro-6-hydroxy-1,5-benzazepin-2,4-dione, and 50 ml of concentrated hydrochloric acid was added thereto. The mixture was heated on a steam bath for 5 hours while stirring. After completion of the reaction, the precipitated crystals were filtered, washed with ethanol, and dried to obtain 26 g of the desired compound.

(8) Synthesis of 9-Chloro-7-(4-methacrylamidobutanamido)-6-hydroxy-1,5-benzazepin-2,4-dione:

In a solution of 38 g of sodium hydroxide, 200 ml of water, and 2 ml of nitrobenzene was dissolved 100 g of γ-aminobutyric acid while stirring, followed by cooling to 0° C. To the aqueous solution were added simultaneously 107.5 g of methacryl chloride and an aqueous solution of 45 g of sodium hydroxide in 100 ml of water. After completion of the reaction, 400 ml of acetonitrile was added thereto. After the reaction mixture was made acidic with 80 ml of concentrated hydrochloric acid, the mixture was extracted with acetonitrile. The resulting acetonitrile extract was concentrated to obtain 149 g of oily N-methacryloyl-γ-aminobutyric acid.

To a mixture of 31.8 g of the resulting N-methacryloyl glycine and 26 g of the 7-amino-9-chloro-6-hydroxy-1,5-benzazepin-2,4-dione hydrochloride as prepared in (7) above were added 53 ml of pyridine and 1 liter of ethyl acetate, followed by stirring under cooling. To the solution was added dropwise 13.6 ml of thionyl chloride. After completion of the reaction, 140 ml of water was added thereto, and the reaction mixture was extracted with ethyl acetate. The extract was concentrated, and acetonitrile was added to the concentrate. The precipitated crystals were recrystallized from acetonitrile to obtain 19 g of the desired monomeric coupler.

(II) Synthesis of Polymeric Coupler (9-chloro-7-(4-methacrylamidobutanamido)-6-hydroxy-1,5-benzazepin-2,4-dione/methacrylic acid/methyl acrylate)

A mixture consisting of 19 g of the monomeric coupler obtained in (I) above, 2.5 g of methacrylic acid, and 125 ml of dioxane was heated to 80° C. in a nitrogen stream while stirring, and 6.25 ml of dioxane containing 350 ml of dimethyl azobisisobutyrate was added thereto to initiate polymerization. After allowing the mixture to react for 5 hours, the reaction mixture was poured into 1 liter of water, and the precipitated crystals were collected by filtration, thoroughly washed with water, and dried by heating under reduced pressure to obtain 29.3 g of the desired polymeric coupler (Coupler 14).

The resulting polymeric coupler was found by colorimetry to contain 49.8 wt % of the monomeric coupler.

Other couplers of the present invention can be synthesized analogously with the procedures described in the foregoing synthesis examples.

The layer containing the cyan coupler according to the present invention or other layers having substantially the same color sensitivity can contain other conventionally known cyan couplers. Cyan couplers which can be used preferably in combination are represented by formula (V)

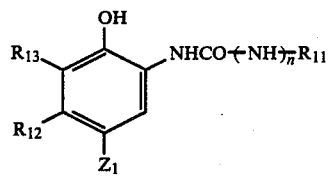

(V)

wherein $R_{11}$ represents a substituted or unsubstituted aliphatic group, a substituted or unsubstituted aryl group, or a substituted or unsubstituted heterocyclic group; $R_{12}$ represents a substituted or unsubstituted aliphatic group, a substituted or unsubstituted aryl group, or a substituted or unsubstituted acylamino group; $R_{13}$ represents a hydrogen atom, a halogen atom, a substituted or unsubstituted aliphatic group, a substituted or unsubstituted aryl group, a substituted or unsubstituted alkoxy group, a substituted or unsubstituted aryloxy group, or a substituted or unsubstituted acylamino group; or $R_{12}$ and $R_{13}$ form a 5- or 6-membered nitrogen-containing heterocyclic group; $Z_1$ represents a hydrogen atom or a group releasable upon coupling with an oxidation product of a developing agent; and n represents 0 or 1, preferably n is 0.

Typical examples of the cyan couplers represented by formula (V) are shown below.

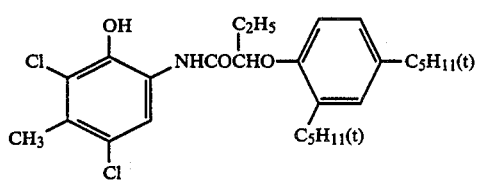

(V-1)

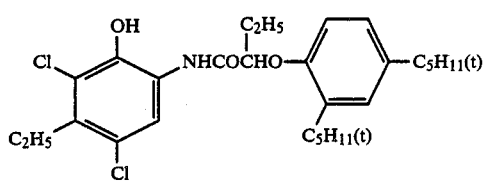

(V-2)

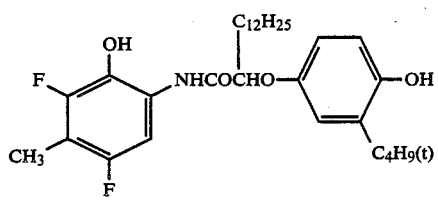

(V-3)

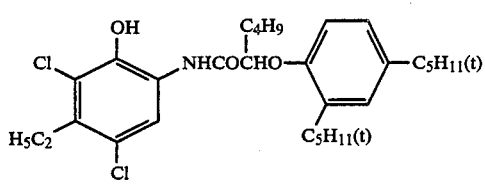

(V-4)

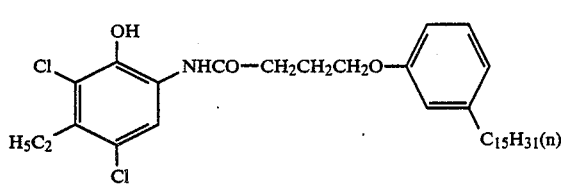

(V-5)

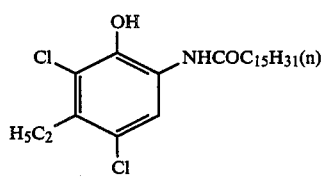

(V-6)

-continued
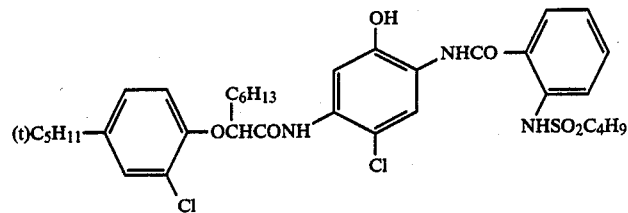
(V-7)
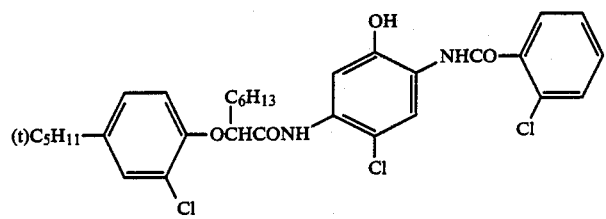
(V-8)
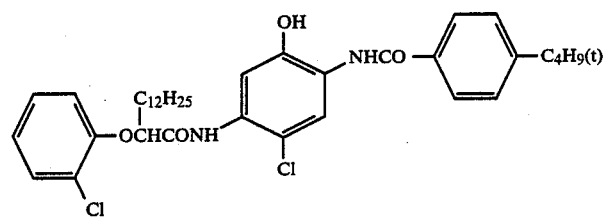
(V-9)
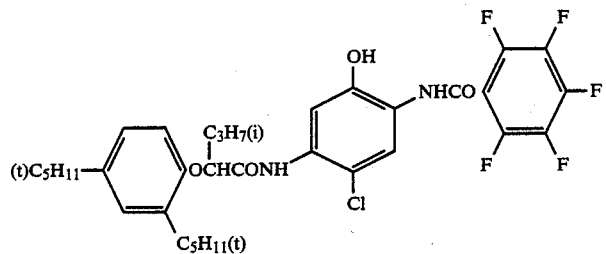
(V-10)
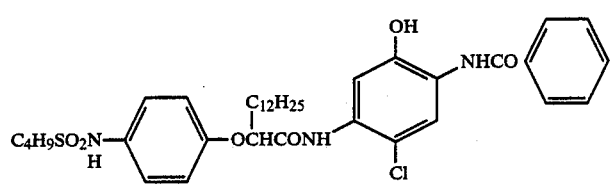
(V-11)
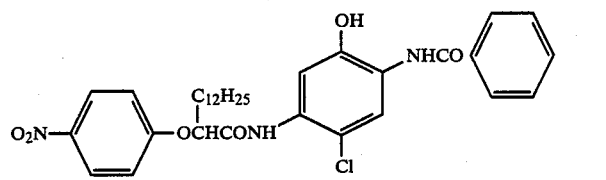
(V-12)
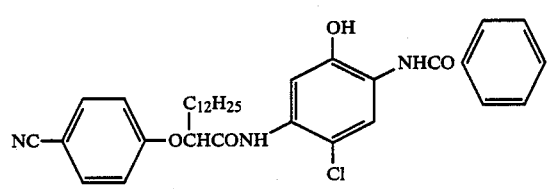
(V-13)

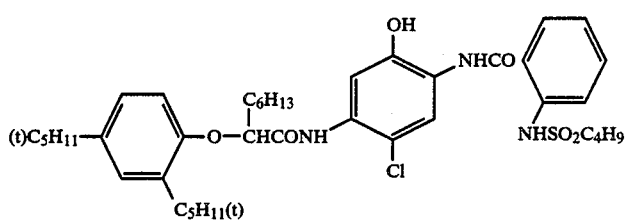
(V-14)
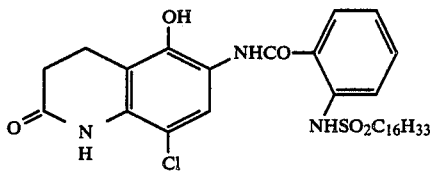
(V-15)
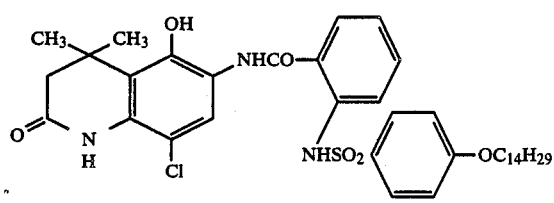
(V-16)
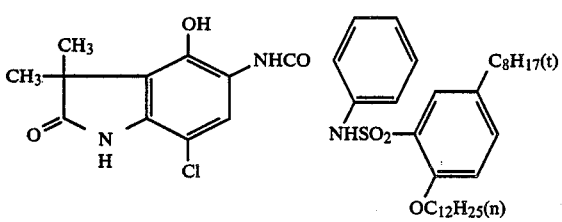
(V-17)
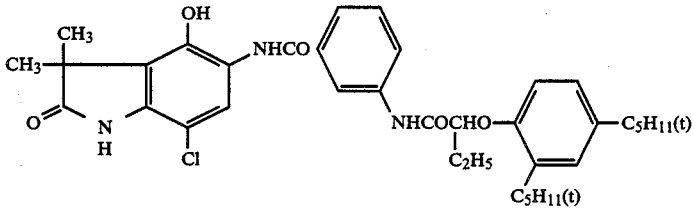
(V-18)
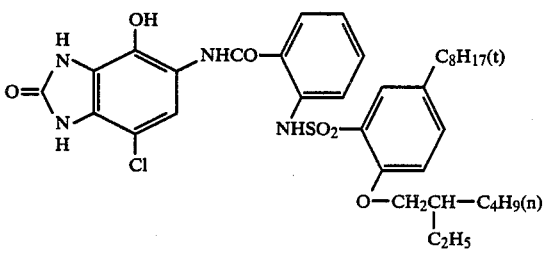
(V-19)
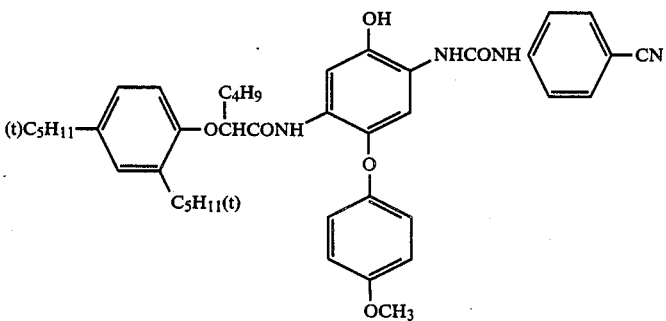
(V-20)

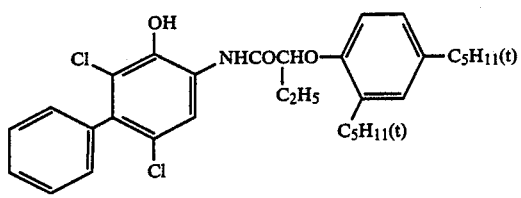
(V-21)

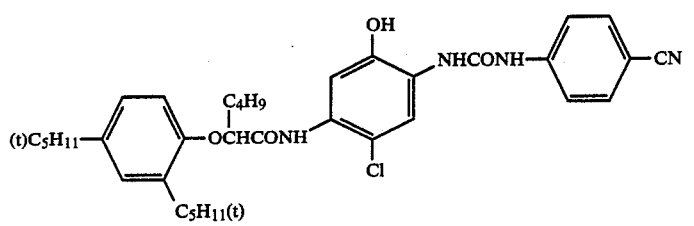
(V-22)

The cyan coupler according to the present invention is present in a silver halide emulsion layer, usually in an amount of from 0.1 to 1.0 mol/m², and preferably from 0.1 to 0.5 mol/m².

The color photographic light-sensitive materials according to the present invention further contains known magenta and yellow couplers in combination with at least one cyan coupler of formula (I).

Typical examples of the yellow couplers which can be used in the invention are described in U.S. Pat. Nos. 2,875,075, 2,407,210, 3,265,506, 2,298,443, 3,048,194, 3,447,928, etc. Among the known yellow couplers, acylacetamide couplers, such as benzoylacetanilides, pivaloylacetanilides, etc., are preferred.

That is, examples of suitable yellow couplers include those represented by formulae (VI) and (VII) shown below.

Formula (VI) is represented by

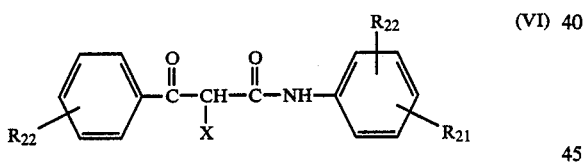
(VI)

wherein $R_{21}$ represents an antidiffusible group having from 8 to 32 total carbon atoms; $R_{22}$ (the two $R_{22}$ groups may be the same or different) represents a hydrogen atom or at least one of a halogen atom, a lower alkyl group, a lower alkoxy group, and an antidiffusible group having from 8 to 32 total carbon atoms; and X represents a hydrogen atom or a group releasable upon coupling (hereinafter up to formula (X), the same).

Formula (VII) is represented by

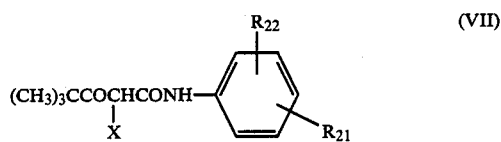
(VII)

wherein $R_{21}$, $R_{22}$ and X are as defined above.

Typical examples of the magenta couplers which can be used in the present invention are described, e.g., in U.S. Pat. Nos. 2,600,788, 2,369,489, 2,343,703, 2,311,082, 3,152,896, 3,519,429, 3,062,653 and 2,908,573, etc. Of the known magenta couplers, preferred are pyrazolone or pyrazoloazole couplers (e.g., pyrazolopyrazoles, pyrazoloimidazoles, pyrazolotriazoles, pyrazolotetrazoles, etc.).

That is, examples of suitable magenta coupler include those represented by the following formulae (VIII), (IX), and (X)

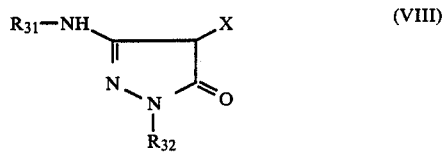
(VIII)

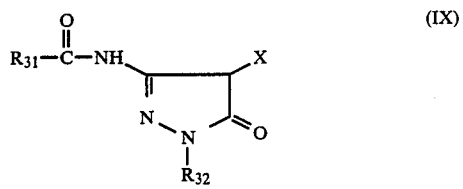
(IX)

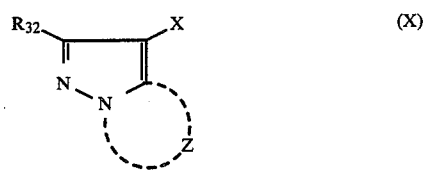
(X)

wherein $R_{31}$ represents an antidiffusible group having from 8 to 32 total carbon atoms; $R_{32}$ represents one or more of a halogen atom, a lower alkyl group, a lower alkoxy group, a phenyl group, and a substituted phenyl group; and Z represents a non-metallic atomic group forming a substituted or unsubstituted 5-membered azole ring (inclusive of a condensed ring) containing from 2 to 4 nitrogen atoms.

The cyan, magenta and yellow couplers can be incorporated in silver halide emulsion layers in a known manner. Details for additives that can be introduced together with the couplers, such as coupler solvents, ultraviolet absorbents, protective colloids, binders, antifoggants, color mixing inhibitors, discoloration inhibitors, sensitizers, dyes, bleaching agents, etc.; methods for preparing silver halide light-sensitive materials, inclusive of preparation of photographic emulsions, introduction of couplers, etc., layer structures, etc.; and photographic processing are described, e.g., in *Research*

*Disclosure*, RD No. 17643 (December, 1978), Japanese Patent Application (OPI) Nos. 65134/81 and 104333/81 (the term "OPI" as used herein referrs to a "published unexamined Japanese patent application") and references cited therein.

In more detail, introduction of the cyan, magenta and yellow couplers in photographic emulsion layers can be carried out by dissolving the coupler in a high boiling point organic solvent having a boiling point of not lower than 160° C. alone or in combination with a low boiling point organic solvent having a boiling point of from 30° C. to 150° C., and emulsifying and dispersing the solution in a hydrophilic colloid aqueous solution. Examples of the high boiling organic solvents that can be used include alkyl phthalates (e.g., dibutyl phthalate, dioctyl phthalate, etc.), phosphoric esters (e.g., diphenyl phosphate, triphenyl phosphate, tricresyl phosphate, dioctylbutyl phosphate, etc.), citric esters (e.g., acetyl tributyl citrate, etc.), benzoic esters (e.g., octyl benzoate, etc.), alkylamides (e.g., diethyllaurylamide, etc.), fatty acid esters (e.g., dibutoxyethyl succinate, dioctyl azelate, Etc.), phenols (e.g., 2,4-di-t-amylphenol, etc.), and the like. Examples of the low boiling organic solvents to be used are lower alkyl acetates (e.g., ethyl acetate, butyl acetate, etc.), sec-butyl alcohol, ethyl propionate, methyl isobutyl ketone, β-ethoxyethyl acetate, methyl cellosolve acetate, and the like.

If desired, the light-sensitive materials of the invention can contain special couplers other than the above-described couplers. For example, a colored magenta coupler can be introduced in a green-sensitive emulsion layer to produce a masking effect. Further, an emulsion layer having the respective color sensitivity or a layer adjacent thereto can contain a coupler capable of releasing a development inhibitor (DIR coupler), a hydroquinone capable of releasing a development inhibitor, and the like. A development inhibitor released from these compounds upon development processing brings about improved image sharpness, improved graininess, or an interlayer effect to increase a monochromatic saturation, etc.

The photographic emulsion layer or a layer adjacent thereto can further contain a coupler capable of releasing a development accelerator or nucleating agent with the progress of silver development to improve photographic sensitivity, graininess, contrast, and the like.

The present invention is applicable to ordinary silver halide color light-sensitive materials, such as color negative films, color papers, color positive films, color reversal films for slides, movies or televisions, and the like.

In ordinary color papers, an ultraviolet absorbent is incorporated in either one, and preferably both, of layers adjacent to a cyan coupler-containing red-sensitive emulsion layer. When the ultraviolet absorbent is added to an intermediate layer between a green-sensitive layer and a red-sensitive layer, it may be co-emulsified with a color mixing inhibitor. When it is added to a protective layer, an additional protective layer may be provided separately as an outermost layer. Such an additional protective layer may contain a matting agent having an appropriate particle size selected depending on the particular circumstances.

The aforesaid ultraviolet absorbent is dissolved in a high boiling organic solvent and/or a low boiling organic solvent, and the solution is dispersed in a hydrophilic colloid similarly to the couplers. The amount of the high boiling organic solvent to be used is not particularly restricted, but it is usually employed in an amount up to 300% by weight based on the ultraviolet absorbent. Use of an organic solvent that is liquid at ambient temperature either alone or in combination with others is preferred.

A combined use of a benzotriazole type ultraviolet absorbent with a combination of couplers according to the present invention is effective to improve preservability, and particularly light fastness, of developed dye images, particularly a cyan image. The ultraviolet absorbent may be co-emulsified with the coupler.

The ultraviolet absorbent is used in an amount sufficient to impart light stability to a cyan dye image. Since too large an amount of the ultraviolet absorbent sometimes causes yellowing of unexposed areas (white background) of color prints, a suitable amount is usually selected from the range of from $1 \times 10^{-4}$ to $2 \times 10^{-3}$ mol/m$^2$, and preferably from $5 \times 10^{-4}$ to $1.5 \times 10^{-3}$ mol/m$^2$.

In order to improve preservability of developed dye images, and particularly a yellow image and a magenta image, various kinds of organic type and metal complex type discoloration inhibitors can be used. The organic discoloration inhibitors include hydroquinones, gallic acid derivatives, p-alkoxyphenols, p-hydroxyphenols, and the like. Dye image stabilizers, stain inhibitors or antioxidants to be used are described in patents cited in *Research Disclosure*, RD No. 17643, VII-I to J. Examples of the metal complex type discoloration inhibitors are described, e.g., in *Research Disclosure*, RD No. 15162 (November, 1976), etc.

In order to improve heat and light fastness of a yellow image, many compounds can be used, including phenols, hydroquinones, hydroxychromans, hydroxycoumarans, hindered amines, and alkyl ethers, silyl ethers or hydrolyzable precursors thereof.

Silver halides which can be used in the silver halide emulsion layers of the invention include silver chloride, silver bromide, silver chlorobromide, silver iodobromide, silver chloroiodobromide, etc. Preferred are silver iodobromide containing from 2 to 20 mol % of silver iodide and silver chlorobromide containing from 10 to 50 mol % of silver bromide. The silver halide grains are not limited in terms of crystal form, crystal structure, grain size, grain size distribution, and the like. For example, they may be regular crystals or twinned, and may have any of hexahedral, octahedral, and tetradecahedral forms. Plate grains having a thickness of not more than 0.5 μm and a diameter of at least 0.6 μm, with an average aspect ratio of 5 or more (i.e., 5/1 or more), as described in *Research Disclosure*, RD No. 22534 (January, 1983), may also be employed.

The crystal structure of silver halide grains may be either homogeneous or heterogeneous. In the latter case, the individual grains may have a core-shell structure of layered structure differing in halogen composition, or an epitaxially grown structure composed of grains differing in halogen composition. The grains may also be composed of various crystal forms. Further, the grains may be either those forming a latent image predominantly on surfaces thereof or those forming a latent image predominantly in the interior thereof.

The silver halides may be selected from fine grains having a diameter of not more than 0.1 μm to giant grains having a projected area diameter reaching 3 μm. Further, silver halide emulsions to be used may be either monodispersed emulsions having a narrow size distribution or polydispersed emulsions having a broad size distribution.

These silver halide grains can be prepared by known processes commonly employed in the art.

The silver halide emulsions may be sensitized by generally employed chemical sensitization, i.e., sulfur sensitization, noble metal sensitization, a combination thereof, etc. The emulsions may also be sensitized to colors of any desired wavelength region by using sensitizing dyes. Dyes which can be used to advantage include methine dyes, e.g., cyanine dyes, hemicyanine dyes, rhodacyanine dyes, merocyanine dyes, oxonol dyes, hemioxonol dyes, etc., and styryl dyes as hereinafter described in detail. These sensitizing dyes may be used either individually or in combinations of two or more thereof.

Supports which can be used in the light-sensitive materials of the invention include transparent supports, such as a polyethylene terephthalate film, a cellulose triacetate film, etc., and reflective supports, such as baryta paper, polyethylene-coated paper, polypropylene synthetic paper, and a transparent support, e.g., a glass plate, a polyester film (e.g., polyethylene terephthalate, cellulose triacetate, cellulose nitrate, etc.), a polyamide film, a polycarbonate film, a polystyrene film, etc., which have provided thereon a reflective layer or a reflector. The reflective supports are preferred. A support to be used can be selected appropriately from among the above-described supports according to the end use.

The blue-, green-, and red-sensitive emulsions to be used in the present invention are obtained by spectrally sensitizing silver halide emulsions with methine dyes and other sensitizing dyes so as to have the respective color sensitivity. Dyes which can be used for spectral sensitization include cyanine dyes, merocyanine dyes, complex cyanine dyes, complex merocyanine dyes, holopolar cyanine dyes, hemicyanine dyes, styryl dyes, and hemioxonol dyes, with cyanine dyes, merocyanine dyes, and complex merocyanine dyes being particularly preferred.

In addition to the above-described layers, the color photographic materials of the invention may further comprise auxiliary layers, such as a subbing layer, an intermediate layer, a protective layer, and so on. If desired, a second ultraviolet absorbing layer may be provided between a red-sensitive silver halide emulsion layer and a green-sensitive silver halide emulsion layer. Ultraviolet absorbents to be used in this layer are preferably selected from the above-mentioned ultraviolet absorbents, but other known ultraviolet absorbents may also be employed.

Binders or protective colloids for the photographic emulsions include gelatin to advantage, but other hydrophilic colloids may also be employed. Examples of the hydrophilic colloids include proteins, such as gelatin derivatives, graft polymers of gelatin with other high polymers, albumin, casein, etc.; cellulose derivatives, such as hydroxyethyl cellulose, carboxymethyl cellulose, cellulose sulfate, etc.; sugar derivatives, such as sodium alginate, starch derivatives, etc.; and a wide variety of synthetic hydrophilic high polymers, such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., and copolymers comprising the monomers constituting these homopolymers.

Gelatin to be used includes not only lime-processed gelatin, but also acid-processed gelatin, enzyme-processed gelatin as described in *Bull. Soc. Photo. Japan*, No. 16, p. 30 (1966), and hydrolysis products or enzymatic decomposition products of gelatin.

The photographic emulsion layers or other hydrophilic colloidal layers may contain brightening agents, such as stilbenes, triazines, oxazoles, coumarins, etc. These brightening agents may be either water-soluble or water-insoluble. In the latter case, they can be used in the form of a dispersion. Specific examples of fluorescent brightening agents are described, e.g., in U.S. Pat. Nos. 2,632,701, 3,269,840 and 3,359,102, British Pat. Nos. 852,075 and 1,319,763, *Research Disclosure*, RD No. 17643 (December, 1978), p. 24 left cols., lines 9-36.

In cases where dyes or ultraviolet absorbents are incorporated in a hydrophilic colloidal layer, the layer may be mordanted with cationic polymers. Examples of the cationic polymers to be used are described, e.g., in British Pat. No. 685,475, U.S. Pat. Nos. 2,675,316, 2,839,401, 2,882,156, 3,048,487, 3,184,309 and 3,445,231, West German Patent Application (OLS) No. 1,914,362, Japanese Patent Application (OPI) Nos. 47624/75 and 71332/75, etc.

The light-sensitive materials may contain hydroquinone derivatives, aminophenol derivatives, gallic acid derivatives, ascorbic acid derivatives, and the like as color fog inhibitors. Specific examples of these color fog inhibitors are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75, and 146235/77, Japanese Patent Publication No. 23813/75, etc.

If desired, the color photographic materials of the invention may further contain various other additives known for photographic use, such as stabilizers, antifoggants, surface active agents, couplers other than those described above, filter dyes, anti-irradiation dyes, developing agents, and the like. Specific examples of these photographic additives are described in *Research Disclosure*, RD No. 17643.

If desired, the silver halide emulsion layers or other hydrophilic colloidal layers may furthermore contain fine silver halide emulsions having no substantial light sensitivity, such as emulsions of silver chloride, silver bromide or silver chlorobromide having a mean grain size of not more than 0.20 μm.

Color developing solutions which can be used in this invention are preferably alkaline aqueous solutions consisting mainly of an aromatic primary amine color developing agent. Typical examples of the color developing agent are 4-amino-N,N-diethylaniline, 3-methyl-4-N,N-diethylaniline, 4-amino-N-ethyl-N-β-hydroxyethylaniline, 3-methyl-4-amino-N-ethyl-β-hydroxyethylanine, 3-methyl-4-amino-N-ethyl-N-β-methanesulfonamidoethylaniline, 4-amino-3-methyl-N-ethyl-N-β-methoxyethyl aniline, etc.

The color developing solution can contain pH buffers, e.g., sulfites, carbonates, borates or phosphates of alkali metals; developing restrainers or antifoggants, e.g., bromides, iodides, and organic antifoggants; and the like. If desired, the developing agents can further contain water softeners, preservatives (e.g., hydroxylamine), organic solvents (e.g., benzyl alcohol, diethylene glycol, etc.), development accelerators (e.g., polyethylene glycol, quaternary ammonium salts, amines, etc.), dye forming couplers, competing couplers, fogging agents (e.g., sodium boron hydride, etc.), auxiliary developing agents (e.g., 1-phenyl-3-pyrazolidone, etc.), tackifiers, polycarboxylic acid chelating agents as described in U.S. Pat. No. 4,083,723, antioxidants as described in West German Patent Application (OLS) No. 2,622,950, and the like.

The amount of benzyl alcohol, if used as a solvent, is preferably not more than 2.0 ml/l, and more preferably not more than 0.5 ml/l. The most preferred developing solution contains no benzyl alcohol at all. The color development is carried out at a temperature between 18° C. and 55° C., preferably 30° C. or more, and more preferably 35° C. or more. The development time preferably ranges from 30 seconds to 2.5 minutes, and more preferably from 45 seconds to 2 minutes. The color development may be followed by washing with water. In the case of continuous development processing, a development solution is preferably replenished with from 160 to 330 ml/m², and preferably not more than 100 ml/m², of a replenisher.

After color development, the photographic emulsion layers are usually subjected to bleaching. Bleaching may be carried out simultaneously with fixation (bleach-fix), or these two steps may be effected separately. Bleaching agents to be used include compounds of polyvalent metals, e.g., iron (III), cobalt (III), chromium (IV), copper (II), etc.; peracids, quinones, nitroso compounds, and the like. Examples of these bleaching agents are ferricyanides; bichromates; organic complex salts of iron (III) or cobalt (III), e.g., complex salts with aminopolycarboxylic acids (e.g., ethylenediaminetetraacetic acid, nitrilotriacetic acid, etc.) or organic acids (e.g., citric acid, tartaric acid, malic acid, etc.); persulfates; permanganates; nitrosophenol; and the like. Of these, potassium ferricyanide, sodium (ethylenediaminetetraacetato)iron (III) and ammonium (ethylenediaminetetraacetato)iron (III) are particularly useful. (Ethylenediaminetetraacetato)iron (III) complex salts are useful in both an independent bleaching bath or a bleach-fix bath.

The bleach-fix processing may be followed by washing with water. The bleach-fix is carried out at a temperature of from 18° C. to 50° C., and preferably 30° C. or higher. When bleach-fix is conducted at a temperature at 35° C. or higher, the time required can be reduced to 1 minute or less and the amount of a replenisher required can be decreased.

Washing after color development or bleach-fix is usually carried out for a period within 3 minutes. Washing may be substantially omitted by using a stabilizing bath.

Developed dyes undergo deterioration or discoloration due to not only light or heat but also mildew generated during preservation. Since cyan images are particularly liable to deterioration due to mildew, use of a mildew-proofing agent is desirable. Specific examples of mildew-proofing agents to be used include 2-thiazolylbenzimidazoles as described in Japanese Patent Application (OPI) No. 157244/82. The mildew-proofing agent may be incorporated in a light-sensitive material per se or may be supplied externally at any stage of development processing by adding to the processing solution.

The invention will now be illustrated in greater detail by way of the following examples. It should be understood, however, that the present invention is not deemed to be limited thereto. In these examples, all the percents are by weight unless otherwise indicated.

EXAMPLE 1

A solution consisting of 10 g of Coupler (1) of the invention, 10 g of dibutyl phthalate, and 20 ml of ethyl acetate was heated to 50° C., and the solution was dispersed in 80 g of a gelatin aqueous solution containing 8 ml of a 1% aqueous solution of sodium dodecylbenzenesulfonate.

The dispersion was mixed with 145 g of a red-sensitive silver chlorobromide emulsion (silver bromide: 50 mol %; silver content: 7 g), and sodium dodecylbenzenesulfonate was added thereto as a coating aid. The resulting coating composition was coated on a paper support laminated with polyethylene on both sides thereof so as to have a coupler coverage of 400 mg/m². Gelatin was then coated thereon to a thickness of 1 g/m² to form a protective layer. The resulting light-sensitive material was designated as Sample (201).

Samples (202) to (213) were prepared in the same manner as for Sample (201) except for replacing Coupler (1) with an equimolar amount of each of the couplers shown in Table 1.

For comparison, Samples (214) to (217) were prepared in the same manner as for Sample (201) except for replacing Coupler (1) with an equimolar amount of each of Comparative Couplers (101) to (104) shown below.

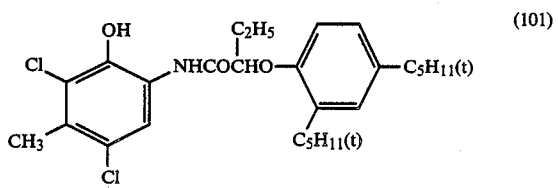

(101)

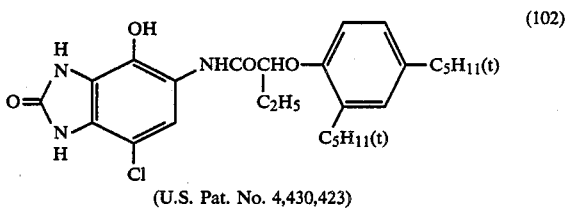

(102)

(U.S. Pat. No. 4,430,423)

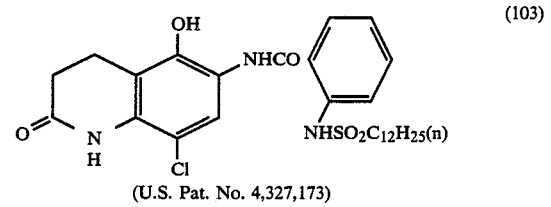

(103)

(U.S. Pat. No. 4,327,173)

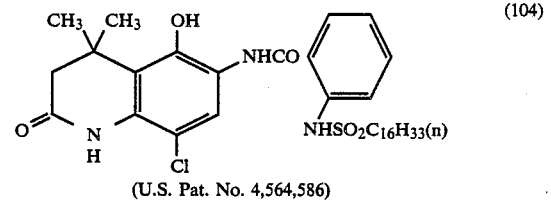

(104)

(U.S. Pat. No. 4,564,586)

Each of the resulting samples was exposed to light through a continuous wedge for sensitometry and then subjected to development processing according to the following procedures:

| Color Development Processing (33° C.): | |
|---|---|
| 1. Color Development | 3 min 30 sec |
| 2. Bleach-Fix | 1 min 30 sec |
| 3. Washing | 2 min 30 sec |

The processing solutions used had the following formulations:

| Formulation of Color Developer: | |
|---|---|
| Benzyl Alcohol | 15.0 ml |
| Diethylene Glycol | 8.0 ml |
| Ethylenediaminetetraacetic Acid | 5.0 g |
| Sodium Sulfite | 2.0 g |
| Anhydrous Potassium Carbonate | 30 g |
| Hydroxylamine Sulfate | 3.0 g |
| Potassium Bromide | 0.6 g |
| 4-Amino-N—ethyl-N—(β-methanesulfonamidoethyl)-m-toluidine Sesquisulfate Monohydrate | 5.0 g |
| Water to make | 1,000 ml (pH = 10.2) |

| Formulation of Bleach-Fix Bath: | |
|---|---|
| Ethylenediaminetetraacetic Acid | 4.0 g |
| (Ethylenediaminetetraacetato)Ferrite | 40 g |
| Sodium Sulfite | 5.0 g |
| Sodium Thiosulfate (70%) | 150 ml |
| Water to make | 1,000 ml |

In order to evaluate fastness of the developed dyes, the samples were allowed to stand in a dark place at 100° C. for 6 days, or at 60° C. and 70% RH for 6 weeks, or were irradiated with light for 6 days in a xenon test (100,000 lux). The fastness of the dye image was expressed in terms of density reduction (%) based on the initial density of 1.0. Yellowing of the white background was expressed in terms of the increase in value density (%) of the unexposed area. The results obtained are shown in Table 1.

TABLE 1

| Sample No. | Coupler | Fastness of Dye Image | | | Yellowing of White Background |
|---|---|---|---|---|---|
| | | 100° C. 6 Days (%) | 60° C., 70% RH 6 Weeks (%) | Light 6 Days (%) | |
| (201) | (1) | 7 | 5 | 8 | +0.09 |
| (202) | (2) | 10 | 9 | 4 | +0.08 |
| (203) | (3) | 8 | 8 | 3 | +0.10 |
| (204) | (4) | 7 | 3 | 5 | +0.07 |
| (205) | (5) | 9 | 4 | 10 | +0.09 |
| (206) | (6) | 6 | 7 | 6 | +0.11 |
| (207) | (9) | 8 | 6 | 7 | +0.10 |
| (208) | (12) | 7 | 8 | 9 | +0.08 |
| (209) | (13) | 9 | 7 | 8 | +0.09 |
| (210) | (14) | 8 | 9 | 5 | +0.09 |
| (211) | (17) | 10 | 8 | 7 | +0.07 |
| (212) | (18) | 6 | 6 | 6 | +0.10 |
| (213) | (19) | 5 | 8 | 8 | +0.08 |
| (214) | (101) | 56 | 53 | 18 | +0.11 |
| (215) | (102) | 10 | 4 | 6 | +0.27 |
| (216) | (103) | 8 | 9 | 20 | +0.31 |
| (217) | (104) | 7 | 6 | 9 | +0.35 |

It can be seen from Table 1 that although the dye images produced from the comparative couplers do exhibit sufficient fastness to heat and light, such couplers tend to undergo serious yellowing of the white background which is a fatal disadvantage to color papers, whereas the couplers according to the present invention exhibit not only excellent fastness to heat and light but also greatly improved resistance to yellowing on the white background.

EXAMPLE 2

Multilayer color photographic materials (Sample Nos. (301) to (314)) were prepared by coating first (the undermost layer) to 7th (the uppermost layer) layers on a paper support laminated with polyethylene on both sides thereof according to the layer structure shown below and in Table 2. The polyethylene layer on the side to be coated contained titanium dioxide as a white pigment and ultramarine as a bluing dye. Each of the coating compositions was prepared as follows, taking Sample (301) as an example.

Preparation of a Coating Composition for the First Layer

To 10 g of Yellow Coupler (a-1) and 2.3 g of Dye Image Stabilizer (b-1) were added 10 ml of ethyl acetate and 4 ml of Solvent (c), and the resulting solution was dispersed in 90 ml of a 10% gelatin aqueous solution containing 5 ml of 10% sodium dodecylbenzenesulfonate. Separately, to a silver chlorobromide emulsion (silver bromide: 80 mol %; silver content: 70 g/kg) was added $4.0 \times 10^{-4}$ mol/mol of silver chlorobromide of a blue-sensitive dye shown below to prepare a blue-sensitive emulsion weighing 90 g. The above prepared dispersion and emulsion were mixed, and its gelatin concentration was adjusted so as to have the composition shown in the following layer structure to prepare a coating composition for the first layer. Coating compositions for the second to seventh layers were prepared in the similar manner. In each layer, a sodium salt of 1-hydroxy-3,5-dichloro-s-triazine was used as a gelatin hardener.

The spectral sensitizers used in the respective emulsion layer were as follows:

Blue-Sensitive Emulsion Layer:

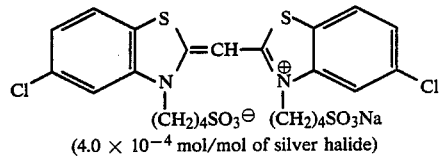

(4.0 × $10^{-4}$ mol/mol of silver halide)

Green-Sensitive Emulsion Layer:

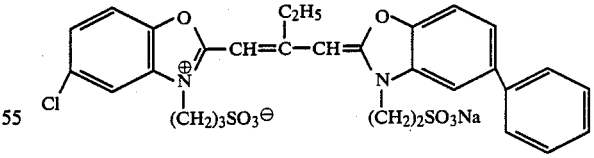

(3.0 × $10^{-4}$ mol/mol of silver halide)

Red-Sensitive Emulsion Layer:

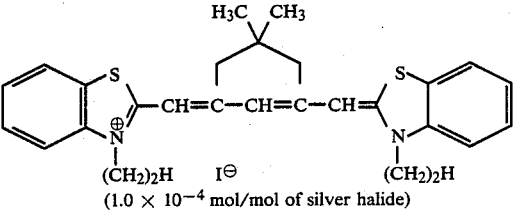

(1.0 × $10^{-4}$ mol/mol of silver halide)

An anti-irradiation dye of formula shown below was used in the green-sensitive emulsion layer.

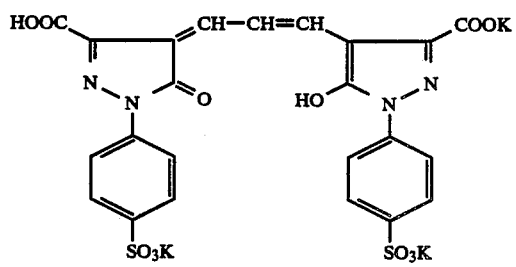

After adjusting a balance between surface tension and viscosity, the coating composition for the first to seventh layers were simultaneously coated on the support.

Layer Structure

Support:
Polyethylene laminated paper in which a white pigment ($TiO_2$, etc.) and a bluing dye are contained at a first layer side.

| First Layer: Blue-Sensitive Layer | |
| --- | --- |
| Silver Chlorobromide Emulsion (silver bromide: 80 mol %) | 0.35 g of Ag/m$^2$ |
| Gelatin | 1.35 g/m$^2$ |
| Yellow Coupler (a) | 6.91 × 10$^{-4}$ mol/m$^2$ |
| Dye Image Stabilizer (b) | 1.38 × 10$^{-4}$ mol/m$^2$ |
| Solvent (c) | 0.02 g/m$^2$ |
| Second Layer: Color Mixing Preventing Layer | |
| Gelatin | 0.70 g/m$^2$ |
| Color Mixing Inhibitor (d) | 2.33 × 10$^{-4}$ mol/m$^2$ |
| Third Layer: Green-Sensitive Layer | |
| Silver Chlorobromide Emulsion (silver bromide: 75 mol %) | 0.15 g of Ag/m$^2$ |
| Gelatin | 1.56 g/m$^2$ |
| Magenta Coupler (e) | 3.38 × 10$^{-4}$ mol/m$^2$ |
| Dye Image Stabilizer (f) | 1.69 × 10$^{-4}$ mol/m$^2$ |
| Solvent (g) | 0.57 g/m$^2$ |
| Fourth Layer: Ultraviolet Absorbing Layer | |
| Gelatin | 1.60 g/m$^2$ |
| Ultraviolet Absorbent (h) | 1.70 × 10$^{-4}$ mol/m$^2$ |
| Color Mixing Inhibitor (i) | 1.60 × 10$^{-4}$ mol/m$^2$ |
| Solvent (j) | 0.27 g/m$^2$ |
| Fifth Layer: Red-Sensitive Layer | |
| Silver Chlorobromide Emulsion (silver bromide: 70 mol %) | 0.22 g of Ag/m$^2$ |
| Gelatin | 0.90 g/m$^2$ |
| Cyan Coupler (k) | 7.05 × 10$^{-4}$ mol/m$^2$ |
| Dye Image Stabilizer (l) | 5.20 × 10$^{-4}$ mol/m$^2$ |
| Solvent (m) | 0.22 g/m$^2$ |
| Sixth Layer: Ultraviolet Absorbing Layer | |
| Gelatin | 0.54 g/m$^2$ |
| Ultraviolet Absorbent (h) | 5.10 × 10$^{-4}$ mol/m$^2$ |
| Solvent (j) | 0.08 g/m$^2$ |
| Seventh Layer: Protective Layer | |
| Gelatin | 1.33 g/m$^2$ |
| Acryl-Modified Polyvinyl Alcohol (degree of modification: 17%) | 0.17 g/m$^2$ |

TABLE 2

| Sample No. | Cyan Coupler (k) | Yellow Coupler (a) | Magenta Coupler (e) | Dye Image Stabilizer (b) | Dye Image Stabilizer (f) | Dye Image Stabilizer (l) | Remarks |
| --- | --- | --- | --- | --- | --- | --- | --- |
| (301) | (1) | (a-1) | (e-1) | (b-1) | (f-1)/(f-2)/(f-3) = 1/1/1* | (l-1)/(l-2)/(l-3) = 1/3/3* | Invention |
| (302) | (2) | " | (e-2) | " | (f-1)/(f-2)/(f-3) = 1/1/1* | (l-1)/(l-2)/(l-3) = 1/3/3* | " |
| (303) | (3) | (a-2) | " | " | (f-1)/(f-2)/(f-3) = 1/1/1* | (l-1)/(l-2)/(l-3) = 1/3/3* | " |
| (304) | (3) | " | (e-3) | " | (f-1) | (l-1)/(l-2)/(l-3) = 1/3/3* | " |
| (305) | (3) | (a-4) | (e-4) | (b-2) | (f-4)/(f-5) = 1/1* | (l-4) | " |
| (306) | (1)/(k-1) = 1/1* | (a-3) | (e-3) | (b-1) | (f-1) | " | " |
| (307) | (3)/(k-2) = 1/1* | (a-2) | (e-2) | " | (f-1)/(f-2)/(f-3) = 1/1/1* | " | " |
| (308) | (3)/(k-2) = 1/1* | " | (e-3) | " | (f-1) | (l-1)/(l-2)/(l-3) = 1/3/3* | " |
| (309) | (3)/(k-3) = 1/1* | (a-4) | (e-4) | (b-2) | (f-1)/(f-5) = 1/1* | (l-4) | " |
| (310) | (101) | (a-1) | (e-1) | (b-1) | (f-1)/(f-2)/(f-3) = 1/1/1* | (l-1)/(l-2)/(l-3) = 1/3/3* | Comparison |
| (311) | (k-1) | " | " | " | (f-1)/(f-2)/(f-3) = 1/1/1* | (l-1)/(l-2)/(l-3) = 1/3/3* | " |
| (312) | " | (a-2) | (e-2) | " | (f-1)/(f-2)/(f-3) = 1/1/1* | (l-1)/(l-2)/(l-3) = 1/3/3* | " |
| (313) | (k-1)/(k-2) = 1/1* | (a-3) | (e-3) | " | (f-1) | (l-4) | " |
| (314) | (k-1)/(k-2) = 1/1* | (a-2) | (e-2) | " | (f-1)/(f-2)/(f-3) = 1/1/1* | (l-1)/(l-2)/(l-3) = 1/3/3* | " |

*Molar ratio

The compounds used in the preparation of Samples (301) to (314) are shown below.

Yellow Coupler (a-1):
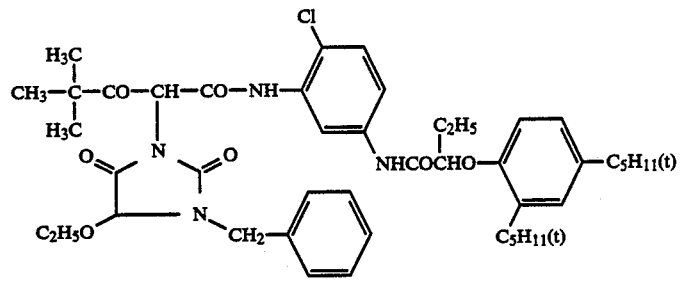
Yellow Coupler (a-2):
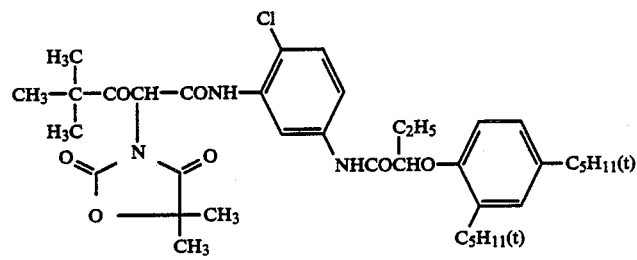
Yellow Coupler (a-3):
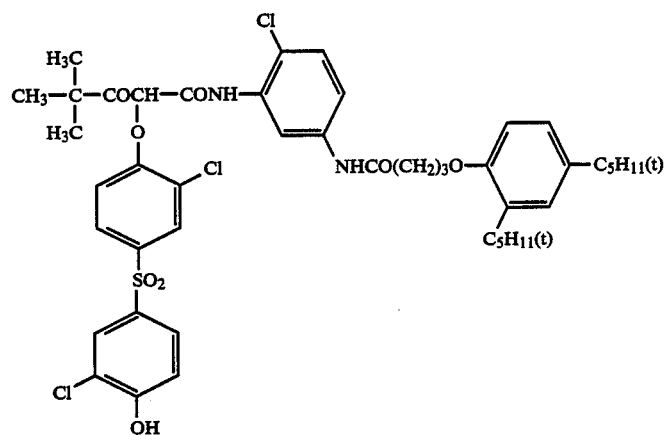
Yellow Coupler (a-4):
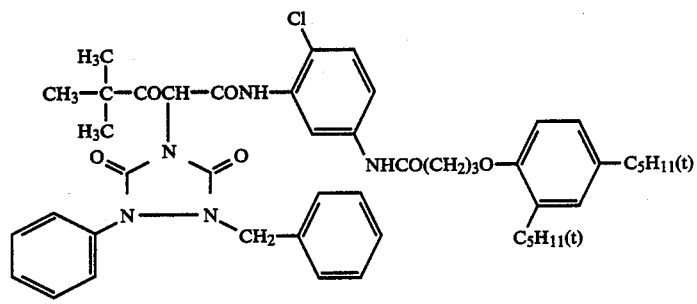
Dye Image Stabilizer (b-1):
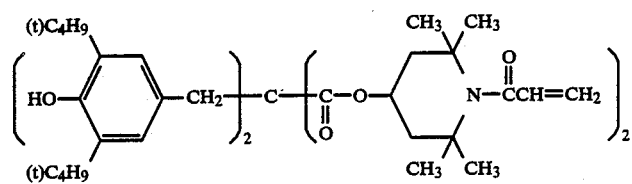

Dye Image Stabilizer (b-2):
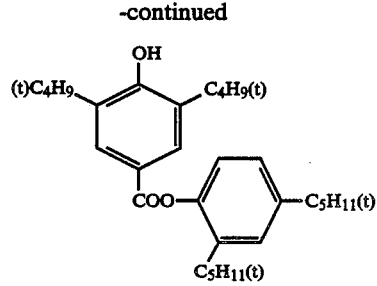
Solvent (c):
Color Mixing Inhibitor (d):
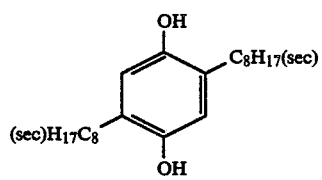
Magenta Coupler (e-1):
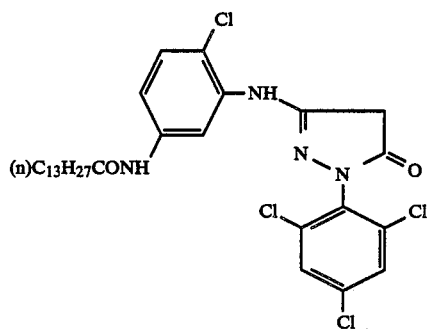
Magenta Coupler (e-2):
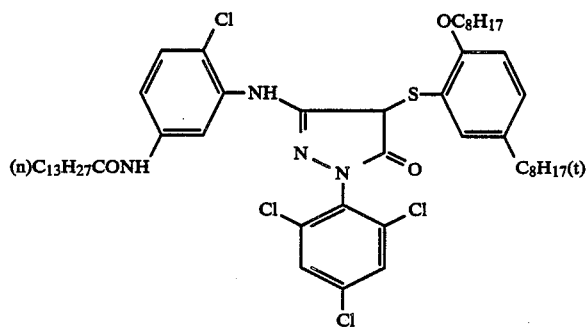
Magenta Coupler (e-3):
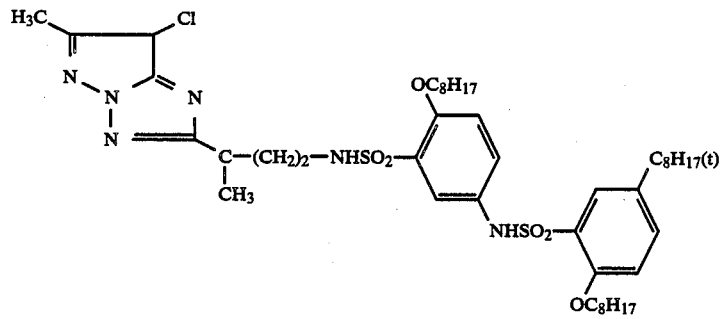

-continued
Magenta Coupler (e-4):
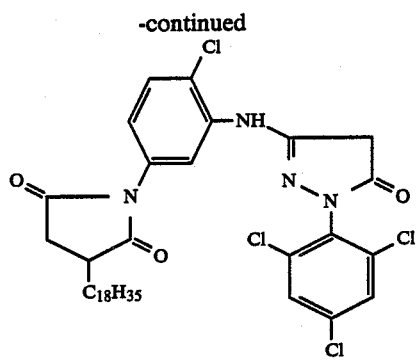
Dye Image Stabilizer (f-1):
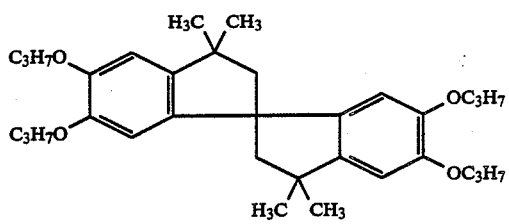
Dye Image Stabilizer (f-2):
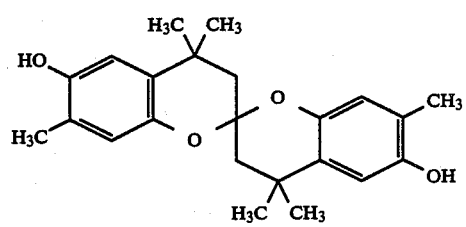
Dye Image Stabilizer (f-3):
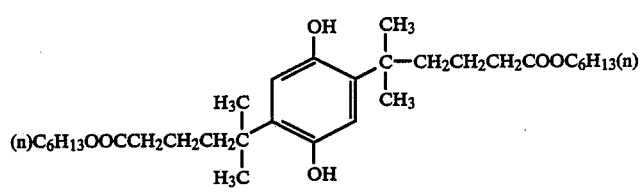
Dye Image Stabilizer (f-4):
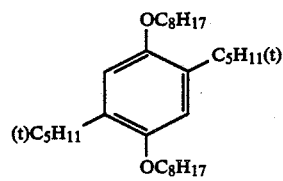
Dye Image Stabilizer (f-5):
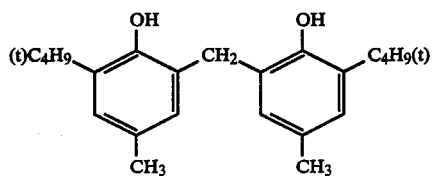
Solvent (g):
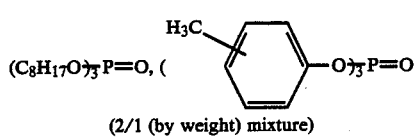
(2/1 (by weight) mixture)
Ultraviolet Absorbent (h):
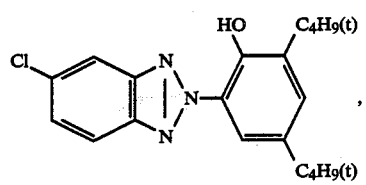

-continued
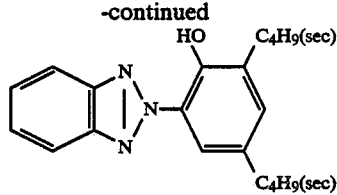
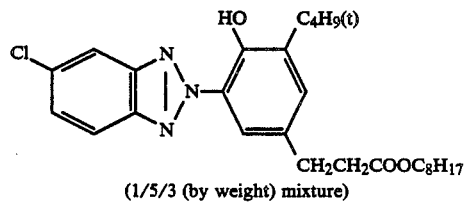
(1/5/3 (by weight) mixture)
Color Mixing Inhibitor (i):
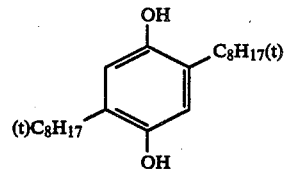
Solvent (j): 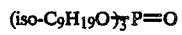
$(iso\text{-}C_9H_{19}O)_3P=O$
Cyan Coupler (k-1):
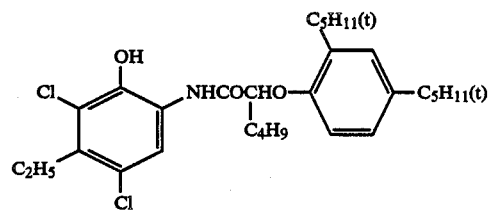
Cyan Coupler (k-2):
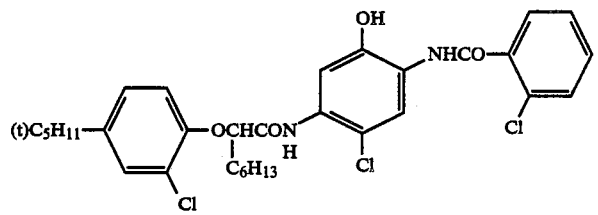
Cyan Coupler (k-3):
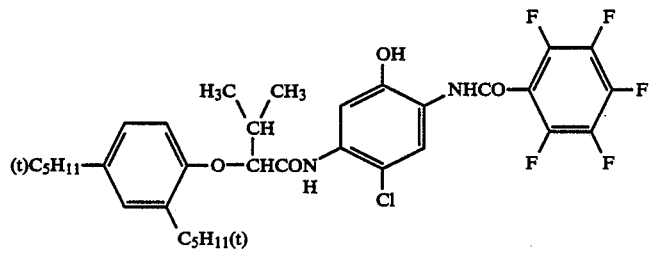
Dye Image Stabilizer (l-1):
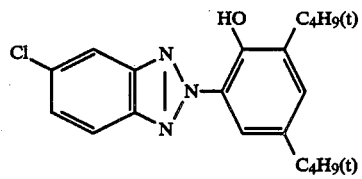
Dye Image Stabilizer (l-2):
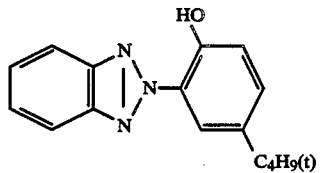

Dye Image Stabilizer (I-3):

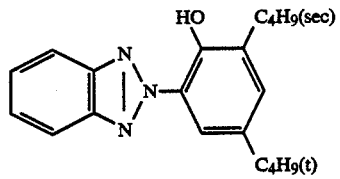

Dye Image Stabilizer (I-4):

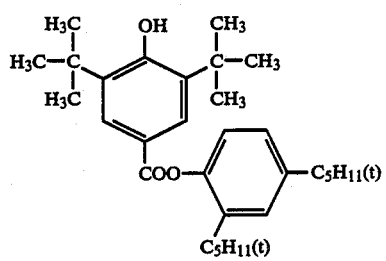

Solvent (m): (iso-$C_9H_{19}O$)$_3$P=O

Each of the resulting samples was wedgewise exposed to light for sensitometry and then subjected to development processing according to the following procedures.

| Step | Temperature (°C.) | Time |
|---|---|---|
| Color Development | 33 | Hereinafter described |
| Bleach-Fix | 33 | 1 min 30 sec |
| Washing | 24-34 | 3 min |
| Drying | 80 | 1 min |

Each of the processing solutions used had the following formulation.

| Color Developer (A): (development time: 3.5 minutes) | |
|---|---|
| Water | 800 ml |
| Diethylenetriaminepentaacetic Acid | 3.0 g |
| Benzyl Alcohol | 15 ml |
| Diethylene Glycol | 10 ml |
| Sodium Sulfite | 2.0 g |
| Potassium Bromide | 0.5 g |
| Potassium Carbonate | 30.0 g |
| N—Ethyl-N—(β-methanesulfonamidoethyl)-3-methyl-4-aminoaniline Sulfate | 5.0 g |
| Hydroxylamine Sulfate | 4.0 g |
| Fluorescent Brightening agent (4,4'-distilbene type) | 1.0 g |
| Water to make | 1,000 ml |
| pH (at 25° C.) | 10.10 |

Color Developer (B): (development time: 2 minutes)

The same as Color Developer (A) except for excluding benzyl alcohol.

| Bleach-Fix Bath (A): | |
|---|---|
| Water | 400 ml |
| Ammonium Thiosulfate (70%) | 150 ml |
| Sodium Sulfite | 18 g |
| Ammonium (Ethylenediaminetetraacetato)-Iron (III) | 55 g |
| Disodium Ethylenediaminetetraacetate | 5 g |

Bleach-Fix Bath (B):
The same as Bleach-Fix Bath (A) except for further containing 30 ml of Color Developer (A).

Bleach-Fix Bath (C):
Bleach-Fix Bath (A) having been fatigued from continuous processing of Fuji Color Paper (produced by Fuji Photo Film Co., Ltd.) by the use of an automatic developing machine until the composition became in a steady state.

Each of the thus processed samples was measured for maximum density ($D_{max}$) by means of a Macbeth densitometer Status AA Filter. The results obtained are shown in Tables 3 and 4.

TABLE 3

| Sample No. | Color Developer (A) Bleach-Fix Bath (A) | Color Developer (B) Bleach-Fix Bath (A) | Remark |
|---|---|---|---|
| (301) | 2.88 | 2.85 | Invention |
| (302) | 3.02 | 2.99 | " |
| (303) | 3.01 | 2.97 | " |
| (304) | 3.00 | 2.96 | " |
| (305) | 2.99 | 2.98 | " |
| (306) | 2.86 | 2.84 | " |
| (307) | 2.95 | 2.93 | " |
| (308) | 2.96 | 2.94 | " |
| (939) | 2.89 | 2.88 | " |
| (310) | 2.89 | 2.53 | Comparison |
| (311) | 2.85 | 2.36 | " |
| (312) | 2.83 | 2.33 | " |
| (313) | 2.78 | 2.21 | " |
| (314) | 2.76 | 2.22 | " |

TABLE 4

| Sample No. | Color Developer (A) Bleach-Fix Bath (A) | Bleach-Fix Bath (B) | Bleach-Fix Bath (C) | Remark |
|---|---|---|---|---|
| (301) | 2.88 | 2.82 | 2.81 | Invention |
| (302) | 3.02 | 3.00 | 2.98 | " |
| (303) | 3.01 | 3.00 | 2.99 | " |
| (304) | 3.00 | 2.98 | 2.97 | " |
| (305) | 2.99 | 2.96 | 2.95 | " |
| (306) | 2.86 | 2.84 | 2.83 | " |
| (307) | 2.95 | 2.91 | 2.89 | " |
| (308) | 2.96 | 2.90 | 2.87 | " |
| (309) | 2.89 | 2.88 | 2.88 | " |
| (310) | 2.89 | 2.51 | 2.47 | Comparison |
| (311) | 2.85 | 2.59 | 2.50 | " |
| (312) | 2.83 | 2.57 | 2.50 | " |
| (313) | 2.78 | 2.69 | 2.65 | " |
| (314) | 2.76 | 2.70 | 2.68 | " |

As can be seen from Table 3, Comparative Samples (310) to (314) undergo significant reduction in color developability when processed with Color Developer (B) containing no benzyl alcohol, while Samples (301) to (309) according to the present invention exhibit sufficient color developability without substantial reduction in density and gamma.

Further, the results of Table 4 demonstrate that the samples according to the present invention suffer from lesser reduction in cyan density when processed with a fatigued bleach-fix bath as compared with the comparative samples.

EXAMPLE 3

Each of Samples (301), (302), (304), (308), and (310) as prepared in Example 2 was exposed to light in the same manner as in Example 2, and then subjected to development processing according to the following procedures.

| Step | Temperature (°C.) | Time |
| --- | --- | --- |
| Color Development | 36 | 45 sec |
| Bleach-Fix | 36 | 45 sec |
| Rinsing (1) | 30 | 20 sec |
| Rinsing (2) | 30 | 20 sec |
| Rinsing (3) | 30 | 20 sec |
| Rinsing (4) | 30 | 20 sec |
| Drying | 70 | 1 min |

The processing solutions used in this example had the following formulations.

Color Developer (B):
The same as Color Developer (B) as in Example 2.
Bleach-Fix Bath (A):
The same as Bleach-Fix Bath (A) as in Example 2.

| Rinsing Solution: | |
| --- | --- |
| Benzotriazole | 1.0 g |
| Ethylenediaminetetramethylene-phosphonic Acid | 0.5 g |
| Potassium Hydroxide | Adequate amount for pH adjustment |
| Water to make | 1,000 ml (pH: 7.5) |

In order to evaluate fastness of the thus-developed cyan, magenta and yellow dye images, the processed samples were allowed to stand in a dark place at 100° C. for 12 days or irradiated with light for 12 days in a xenon tester (100,000 lux), and the rates of reduction in cyan, magenta and yellow densities ($D_R$, $D_G$ and $D_B$, respectively) based on the initial density of 1.0 were determined. The results obtained are shown in Table 5 below.

TABLE 5

| Sample No. | 100° C., 12 Days | | | Light, 12 Days | | | Remark |
| --- | --- | --- | --- | --- | --- | --- | --- |
| | $D_B$ (%) | $D_G$ (%) | $D_R$ (%) | $D_B$ (%) | $D_G$ (%) | $D_R$ (%) | |
| (301) | 4 | 6 | 6 | 10 | 15 | 7 | Invention |
| (302) | 5 | 7 | 7 | 10 | 13 | 5 | " |
| (304) | 4 | 6 | 8 | 8 | 10 | 7 | " |
| (308) | 4 | 7 | 5 | 9 | 11 | 6 | " |
| (310) | 4 | 6 | 45 | 11 | 16 | 20 | Comparison |

As can be seen from Table 5, the samples in accordance with the present invention exhibit fastness to light and heat and maintain a good balance of three colors.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having provided thereon at least one silver halide emulsion layer containing a cyan-dye-forming coupler represented by formula (I)

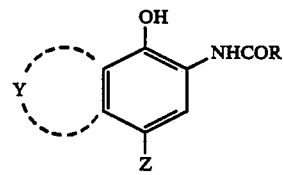

wherein Y represents an atomic group forming an at least 7-membered nitrogen-containing heterocyclic ring containing at least one —NHCO— group; Z represents a hydrogen atom or a group releasable upon coupling with an oxidation product of a color developing agent; R represents an aliphatic group, an aromatic group, a heterocyclic group, or a substituted amino group; or any of R, Z, and Y form a dimer or higher polymer.

2. A silver halide color photographic material as in claim 1, wherein Y includes divalent groups selected from a substituted or unsubstituted amino group, an ether linkage, a thiol linkage, a substituted or unsubstituted alkylene group, an ethylene linkage, an imino linkage, a substituted or unsubstituted sulfonyl group, a carboxyl group, and a group represented by formula

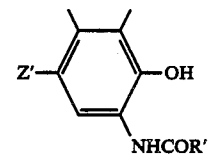

wherein Z' has the same meaning as Z; and R' has the same meaning as R.

3. A silver halide color photographic material as in claim 1, wherein Z represents a hydrogen atom, a halogen atom, a aryloxy group, an alkoxy group, or a sulfonamido group.

4. A silver halide color photographic material as in claim 3, wherein Z represents a fluorine atom or a chlorine atom.

5. A silver halide color photographic material as in claim 1, wherein said cyan-dye-forming coupler is represented by formula (II)

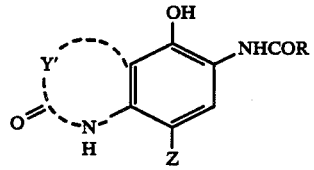

wherein Y' represents an atomic group forming an at least 7-membered nitrogen-containing heterocyclic ring together with the atomic group to which Y' is bonded;

and R and Z each has the same meaning as defined in claim 1,
or formula (III)

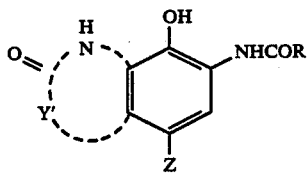

wherein R, Z and Y' are the same as defined above.

6. A silver halide color photographic material as in claim 1, wherein said cyan-dye-forming coupler is represented by formula (IV)

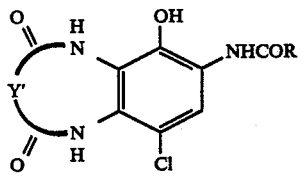

wherein Y" represents an atomic group forming a 7- to 16-membered nitrogen-containing heterocyclic ring together with the atomic group to which Y" is bonded; and R has the same meaning as defined in claim 1.

7. A silver halide color photographic material as in claim 6, wherein Y" represents

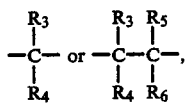

wherein $R_3$, $R_4$, $R_5$ and $R_6$ each represents a hydrogen atom, a halogen atom, an alkyl group, an aryl group, an alkyloxy group, an alkyloxycarbonyl group, an alkoxycarbonyl group, an alkylcarbonyl group, an arylcarbonyl group, a carbamoyl group, an acylamino group, or a nitrile group, or $R_3$ and $R_4$, or $R_3$ and $R_5$ together form a ring or a double bond, or $R_3$, $R_4$, $R_5$ and $R_6$ together form an aromatic ring.

8. A silver halide color photographic material as in claim 1, wherein said silver halide containing a cyan-dye-forming coupler represented by formula (I) also comprises one or more cyan couplers represented by formula (V)

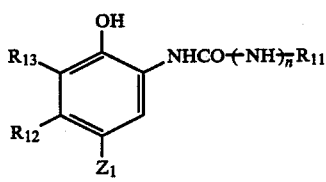

wherein $R_{11}$ represents a substituted or unsubstituted aliphatic group, a substituted or unsubstituted aryl group, or a substituted or unsubstituted heterocyclic group; $R_{12}$ represents a substituted or unsubstituted aliphatic group, a substituted or unsubstituted aryl group, or a substituted or unsubstituted acylamino group; $R_{13}$ represents a hydrogen atom, a halogen atom, a substituted or unsubstituted aliphatic group, a substituted or unsubstituted aryl group, a substituted or unsubstituted alkoxy group, a substituted or unsubstituted aryloxy group, or a substituted or unsubstituted acylamino group; or $R_{12}$ and $R_{13}$ form a 5- or 6-membered nitrogen-containing heterocyclic group; $Z_1$ represents a hydrogen atom or a group releasable upon coupling with an oxidation product of a developing agent; and n represents 0 or 1.

9. A silver halide color photographic material as in claim 8, wherein n of formula (V) is 0.

10. A silver halide color photographic material as in claim 1, wherein said cyan-dye-forming coupler represented by formula (I) is present in said silver halide emulsion layer in an amount of from 0.1 to 0.5 mol/m².

11. A silver halide color photographic material as in claim 2, wherein said cyan-dye-forming coupler represented by formula (I) is present in said silver halide emulsion layer in an amount of from 0.1 to 0.5 mol/m².

12. A silver halide color photographic material as in claim 3, wherein said cyan-dye-forming coupler represented by formula (I) is present in said silver halide emulsion layer in an amount of from 0.1 to 0.5 mol/m².

13. A silver halide color photographic material as in claim 4, wherein said cyan-dye-forming coupler represented by formula (I) is present in said silver halide emulsion layer in an amount of from 0.1 to 0.5 mol/m².

14. A silver halide color photographic material as in claim 5, wherein said cyan-dye-forming coupler represented by formula (II) or (III) is present in said silver halide emulsion layer in an amount of from 0.1 to 0.5 mol/m².

15. A silver halide color photographic material as in claim 6, wherein said cyan-dye-forming coupler represented by formula (IV) is present in said silver halide emulsion layer in an amount of from 0.1 to 0.5 mol/m².

16. A silver halide color photographic material as in claim 7, wherein said cyan-dye-forming coupler represented by formula (IV) is present in said silver halide emulsion layer in an amount of from 0.1 to 0.5 mol/m².

17. A silver halide color photographic material as in claim 8, wherein said cyan-dye-forming coupler represented by formula (I) is present in said silver halide emulsion layer in an amount of from 0.1 to 0.5 mol/m².

18. A silver halide color photographic material as in claim 9, wherein said cyan-dye-forming coupler represented by formula (I) is present in said silver halide emulsion layer in an amount of from 0.1 to 0.5 mol/m².

19. A silver halide color photographic material as in claim 1, which further comprises a yellow coupler of formula (VI) or (VII)

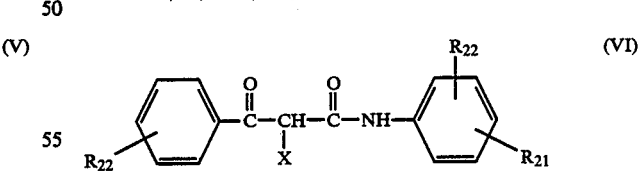

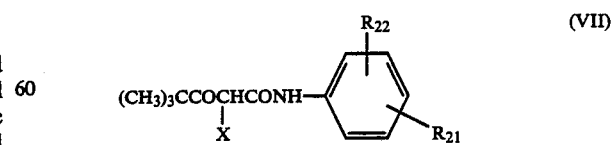

wherein $R_{21}$ represents an antidiffusible group having from 8 to 32 total carbon atoms; $R_{22}$, two of which may be the same or different, represents a hydrogen atom or at least one of a halogen atom, a lower alkyl group, a lower alkoxy group, and an antidiffusible group having from 8 to 32 total carbon atoms; and X represents a hydrogen atom or a group releasable upon coupling.

20. A silver halide color photographic material as in claim 1, which further comprises a magenta coupler of formula (VIII), (IX) or (X)

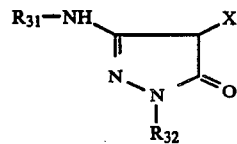

(VIII)

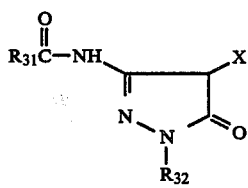

(IX)

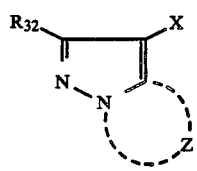

(X)

wherein $R_{31}$ represents an antidiffusible group having from 8 to 32 total carbon atoms; $R_{32}$ represents one or more of a halogen atom, a lower alkyl group, a lower alkoxy group, a phenyl group, and a substituted phenyl group; X represents a hydrogen atom or a group releasable upon coupling; and Z represents a non-metallic atomic group forming a substituted or unsubstituted 5-membered azole ring, inclusive of a condensed ring, containing from 2 to 4 nitrogen atoms.

21. A silver halide color photographic material as in claim 19, which further comprises a magenta coupler of formula (VIII), (IX) or (X)

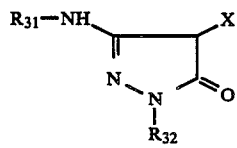

(VIII)

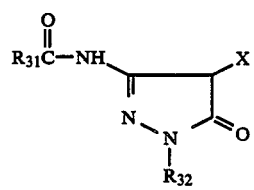

(IX)

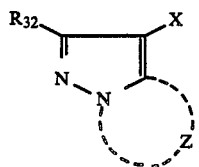

(X)

wherein $R_{31}$ represents an antidiffusible group having from 8 to 32 total carbon atoms; $R_{32}$ represents one or more of a halogen atom, a lower alkyl group, a lower alkoxy group, a phenyl group, and a substituted phenyl group; X represents a hydrogen atom or a group releasable upon coupling; and Z represents a non-metallic atomic group forming a substituted or unsubstituted 5-membered azole ring, inclusive of a condensed ring, containing from 2 to 4 nitrogen atoms.

* * * * *